United States Patent [19]
Alzeer et al.

[11] Patent Number: 6,084,120
[45] Date of Patent: Jul. 4, 2000

[54] β-ALKOXYACRYLATES AGAINST MALARIA

[75] Inventors: Jawad Alzeer; Jacques Chollet, both of Basel, Switzerland; Christian Hubschwerlen, Durmenach, France; Hugues Matile, Basel; Robert George Ridley, Birsfelden, both of Switzerland

[73] Assignee: Hoffmann-La Roche Inc., Nutley, N.J.

[21] Appl. No.: 09/102,463

[22] Filed: Jun. 22, 1998

[30]   Foreign Application Priority Data

Jul. 9, 1997   [EP]   European Pat. Off. ............... 97111607

[51] Int. Cl.$^7$ ...................... C07C 255/50; C07C 229/34; C07D 253/08; C07D 333/72
[52] U.S. Cl. ........................... 558/414; 544/183; 546/173; 546/342; 548/187; 548/572; 549/58; 549/79; 549/499; 560/125; 560/127; 562/507; 562/510
[58] Field of Search ..................................... 560/125, 127; 562/510, 507; 544/183; 558/414; 546/173, 342; 548/187, 572; 549/58, 79, 499

[56]   References Cited

U.S. PATENT DOCUMENTS

| | | |
|---|---|---|
| 4,723,034 | 2/1988 | Schirmer et al. . |
| 5,118,710 | 6/1992 | Wingert et al. . |
| 5,334,607 | 8/1994 | Sauter et al. . |
| 5,356,931 | 10/1994 | Kirstgen et al. . |
| 5,376,677 | 12/1994 | Trah . |
| 5,389,619 | 2/1995 | Doetzer et al. . |
| 5,409,954 | 4/1995 | Kirstgen et al. . |
| 5,563,168 | 10/1996 | Brand et al. . |

FOREIGN PATENT DOCUMENTS

| | | |
|---|---|---|
| 178 826 | 10/1985 | European Pat. Off. . |
| 254 426 | 6/1987 | European Pat. Off. . |
| 278 595 | 1/1988 | European Pat. Off. . |
| 299 694 | 7/1988 | European Pat. Off. . |
| 370 629 | 10/1989 | European Pat. Off. . |
| 379 098 | 1/1990 | European Pat. Off. . |
| 433 233 | 12/1990 | European Pat. Off. . |
| 460 575 | 6/1991 | European Pat. Off. . |
| 463 488 | 6/1991 | European Pat. Off. . |
| 474 042 | 8/1991 | European Pat. Off. . |
| 475 158 | 8/1991 | European Pat. Off. . |
| 0 515 901 A1 | 5/1992 | European Pat. Off. . |
| 2 670 782 | 6/1992 | France . |
| 35 19 280 A1 | 12/1986 | Germany . |
| 90 07493 | 7/1990 | WIPO . |

OTHER PUBLICATIONS

Derwent Abstract: FR 2670781A.
Derwent Abstract: WO 9007493A.
Derwent Abstract: EP 460575A.

*Primary Examiner*—Joseph McKane
*Assistant Examiner*—Taofiq A. Solola
*Attorney, Agent, or Firm*—George W. Johnston; Patricia S. Rocha-Tramaloni; Eileen M. Ebel

[57]   ABSTRACT

The present invention relates to compounds having the formulae

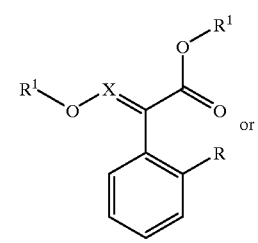

IA

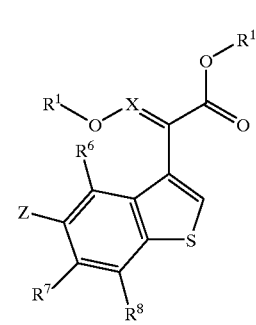

IB wherein R, $R^1$, $R^6$, $R^7$, $Rn^8$, X, and Z are defined herein, which are useful in the treatment or prophylaxis of malaria. The compounds of the present invention are especially useful in the treatment or prophylaxis of chloroquine-sensitive and chloroquine-resistant malaria.

21 Claims, No Drawings

β-ALKOXYACRYLATES AGAINST MALARIA

The invention relates to compounds of the formulae

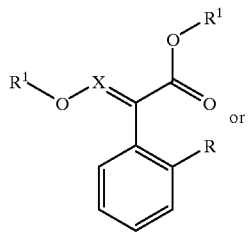

IA or

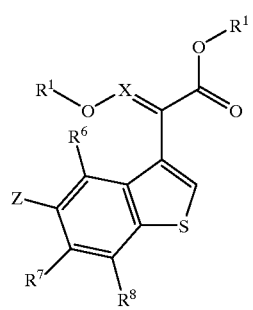

IB wherein
$R^1$ is lower alkyl
X is N or CH

R in IA is

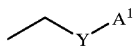

Ia1 wherein
Y is S or O and
$A^1$ is phenyl which is unsubstituted or substituted by one or more substituents selected from halogen, lower alkoxy, lower alkyl, $CF_3$, $NO_2$, $NH_2$, phenoxy or $CF_3$-phenoxy; naphthyl; isothiazol-3-yl; thiazol-2-yl which is unsubstituted or substituted by lower alkoxy-alkoxyalkyl, lower alkyl, lower alkoxycarbonyl or lower acetoxyalkyl; thiadiazol-2-yl which is unsubstituted or substituted by lower alkylthio, lower alkinylthio, cycloalkyl-alkylthio, $CF_3$ or $-NHC_6H_4CF_3$; quinoxalin-2-yl which is unsubstituted or substituted by halogen or lower alkyl; benzoxazol-2-yl; benzotriazine which is unsubstituted or substituted by an oxo-group; and quinolin-2-yl;

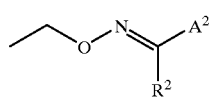

Ia2 wherein
$R^2$ is hydrogen, lower alkoxycarbonyl, $CF_3$, lower alkyl, cycloalkyl, lower alkoxyalkyl, lower alkylthioalkyl or lower alkoxy; and
$A^2$ is phenyl which is unsubstituted or substituted by one or more substituents selected from lower alkyl, $CF_3$, halogen, lower alkylthio, lower alkoxy or $NO_2$; —C(O)$C_6H_5$; —C(CH$_3$)=CH—C$_6H_4$-lower alkyl; —CH=CH—$C_6H_5$; pyridin-2-yl; pyridin-3-yl; pyridin-4-yl; thiazol-5-yl which is unsubstituted or substituted by lower alkyl; thien-3-yl which is unsubstituted or substituted by lower alkyl; thien-2-yl which is unsubstituted or substituted by halogen; quinolin-2-yl; naphthyl; benzo[b]thiophen-2-yl, which is unsubstituted or substituted by lower alkyl or halogen; or benzo[b]furan-2-yl;

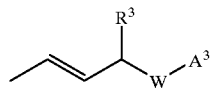

Ia3 wherein
W is S, O, NH or $CH_2$;
$R^3$ is hydrogen or lower alkyl; and
$A_3$ is 5-acetoxy-6-acetoxymethyl-5,6-dihydro-2H-pyran or phenyl which is unsubstituted or substituted by one or more substituents selected from halogen, $CF_3$ or lower alkyl;

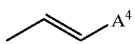

Ia4 wherein
$A^4$ is phenyl which is unsubstituted or substituted by one or more substituents selected from $NO_2$, lower alkoxy, halogen, $CF_3$, phenyloxy, styryl-phenyl or (2-$CF_3$- or Cl-phenyl)-furan-2-yl; benzo[1,3]dioxol-5-yl which is unsubstituted or substituted by halogen; isoxazol-4-yl which is unsubstituted or substituted by phenyl or lower alkoxy-alkoxy; quinolin-3-yl; pyridin-2-yl; pyridin-3-yl; pyridin-4-yl; furyl; thien-2-yl; thien-3-yl; —C≡C—C(CH$_3$)$_3$; —C≡C—C$_6H_5$; indolizin-2-yl which is unsubstituted or substituted by lower alkyl; benzofuran-2-yl; benzopyran-3-yl or dihydrobenzo[b]thiophen-5-yl;

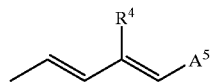

Ia5 wherein
$R^4$ is hydrogen or lower alkyl; and
$A^5$ is phenyl substituted by one or more substituents selected from lower alkyl, lower alkoxy, $NO_2$, halogen, cyano or $CF_3$; pyridin-2-yl; pyridin-4-yl; quinolin-2-yl; quinolin-3-yl; naphthyl; pyrrol-2-yl substituted by lower alkyl; furan-2-yl; furan-3-yl; thien-2-yl; thien-3-yl which is unsubstituted or substituted by halogen and lower alkyl; thiazol-2-yl which is unsubstituted or substituted by $C_6H_4$Cl; thiazol-4-yl which is unsubstituted or substituted by phenyl; benzo[b]thiophen-2-yl which is unsubstituted or substituted by halogen; or benzo[b]thiophen-3-yl;

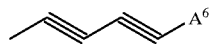

Ia6 wherein $A^6$ is phenyl which is unsubstituted or substituted by $CF_3$;

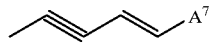
Ia7 wherein
$A^7$ is phenyl which is unsubstituted or substituted by $CF_3$;
or —$(CH_2)_n$-$A^8$ Ia8
wherein
n is 4 and
$A^8$ is phenyl which is unsubstituted or substituted by one or more substituents selected from $CF_3$, halogen or —CH=N—$OCH_2$-CO—$OCH_3$; naphthyl; or pyridin-4-yl;

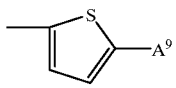
Ia9 wherein
$A^9$ is phenyl which is unsubstituted or substituted by $CF_3$;
and wherein in formula IB each of
$R^6$, $R^7$
and $R^8$ are hydrogen, lower alkyl or lower alkoxy and
Z is hydrogen; lower alkoxy; lower alkyl; or halogen

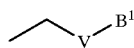
Ib1 wherein
V is O, —N($CH_3$)—, —S— and
$B^1$ is phenyl which is unsubstituted or substituted by halogen or alkyl; quinolin-8-yl; pyrimidin-2-yl; —CH($CH_3$)—$C_6H_5$; or —$CH_2$—$C_6H_5$;

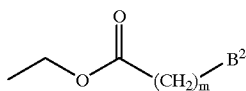
Ib2 wherein
m is 0 or 1; and
$B^2$ is phenyl which is unsubstituted or substituted by halogen, lower alkyl or $CF_3$; or benzo[b]thiophen-5-yl;

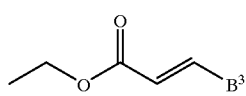
Ib3 wherein
$B^3$ is phenyl which is unsubstituted or substituted by $CF_3$;

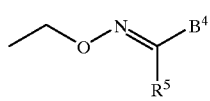
Ib4 wherein
$R^5$ is hydrogen, lower alkyl or lower alkoxyalkyl and $B^4$ is phenyl which is unsubstituted or substituted by $CF_3$; pyridin-2-yl; or thiazolin-5-yl which is unsubstituted or substituted by lower alkyl;

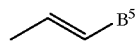
Ib5 wherein
$B^5$ is phenyl; —C≡C—C($CH_3$)$_3$; or thien-3-yl; the stereoisomers and racemates thereof; and the pharmaceutically acceptable salts of compounds of formulae IA and IB.

It has now surprisingly been found that compounds of the present invention are useful against malaria. Every year, between 300 and 500 million people develop malaria. Close to 3 million people die as a result of this disease, most of them children and nearly all of them living in tropical Africa. Fifty years ago, many people thought that malaria could be completely eradicated. But over the past twenty years, malaria has been making a comeback. For years, chloroquine has been the standard treatment, but in some areas the malaria parasite is resistant to chloroquine and to cocktails of almost all the older antimalarials. Around 40% of the world's population now live in areas where malaria is found.

The compounds of the invention have the property that they are active not only against chloroquine-sensitive, but also against chloroquine-resistant malaria pathogens. For this reason they are very well suited for the prophylaxis and treatment of malaria, especially in cases where the malaria pathogens are resistant to chloroquine.

Most of the above described β-alkoxyacrylates and their salts are known compounds. They are described in the following documents: EP 379 098; EP 299 694; WO 9007493; EP 278 595; EP 463 488; EP 370 629; EP 475 158; EP 474 042; EP 178 826; DE 3 519 280; EP 433 233; EP 460 575 and EP 254 426 as compounds with fungicidal activity for use in agriculture.

The following compounds of formula IA5 are novel:

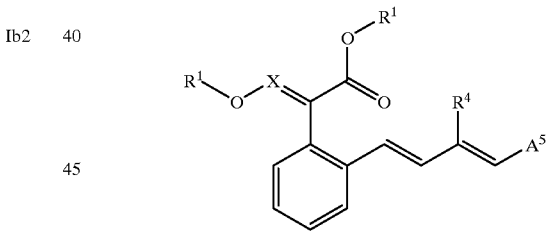
IA5 wherein
$R^1$ is lower alkyl,
X is N or CH,
$R^4$ is hydrogen or lower alkyl and
$A^5$ is phenyl which is unsubstituted or unsubstituted or substituted by one or more substituents selected from lower alkyl, lower alkoxy, $NO_2$, halogen, cyano or $CF_3$; pyridin-2-yl; pyridin-4-yl; quinolin-2-yl; quinolin-3-yl; naphthyl; pyrrol-2-yl which is unsubstituted or substituted by lower alkyl; furan-2-yl, furan-3-yl; thien-2-yl; thien-3-yl which is unsubstituted or substituted by halogen and lower alkyl; thiazol-2-yl which is unsubstituted or substituted by $C_6H_4Cl$; thiazol-4-yl which is unsubstituted or substituted by phenyl; benzo[b]thiophen-2-yl which is unsubstituted or substituted by halogen; or benzo[b]thiophen-3-yl;
as well as their pharmaceutically acceptable salts.

Objects of the present invention are the use of the mentioned compounds of formulae IA and IB and their pharmaceutically acceptable salts thereof against chloroquine-sensitive and chloroquine resistant malaria pathogens, the use of these compounds for making the corresponding medicaments medicaments containing these compounds and their salts as well as new compounds of formula IA5 per se.

The following definitions of the terms used in the present description apply irrespective of whether the terms in question appear alone or in combination.

As used herein, the term "lower alkyl" denotes a straight or branched-chain alkyl group containing from 1–4 carbon atoms, for example, methyl, ethyl, n-propyl, isopropyl, n-butyl, isobutyl, s-butyl, t-butyl and the like.

The term "halogen" denotes chlorine, iodine, fluorine or bromine.

The term "lower alkoxy" denotes an alkyl group, as defined earlier which is attached via an oxygen atom. The term "cycloalkyl" denotes saturated cyclic hydrocarbon residues containing 3 to 6 carbon atoms.

The present invention embraces all possible racemates and their optical antipodes.

Preferred compounds of formula IA are especially those of formula IA5,

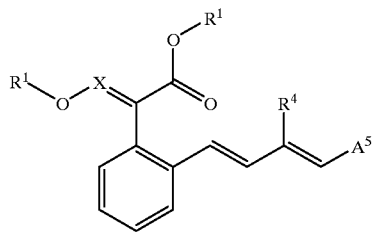

IA5 in which $R^1$ is methyl, X is CH, $R^4$ is hydrogen and $A^5$ is phenyl which is substituted by one or more substituents selected from $CF_3$, bromine, chlorine, methoxy, $NO_2$ or lower alkyl; naphthyl; or thienyl.

Compounds of formula IA2

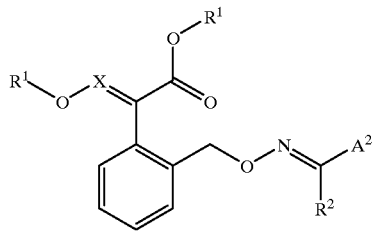

IA2 in which $R^1$ is methyl, X is CH, $R^2$ is hydrogen or lower alkyl and $A^2$ is phenyl which is substituted by $CF_3$, chloro, fluoro, methyl, t-butyl or $SCH_3$ are also preferred.

Another group of preferred compounds is the following:

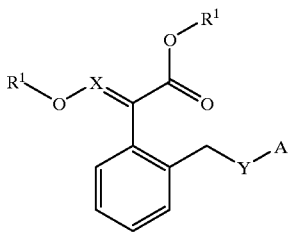

IA1 in which $R^1$ is methyl, X is CH, Y is O or S and $A^1$ is phenyl which is unsubstituted or substituted by methyl, isopropyl, t-butyl, bromo, chloro, $CF_3$ or methoxy; naphthalenyl; or thiadiazolyl which is unsubstituted or substituted by thiomethyl or propynylthiocyclopropyl.

The following intermediates which are used in the process for preparation of compounds of formulae IA4 show also a pharmaceutical activity against malaria pathogens:

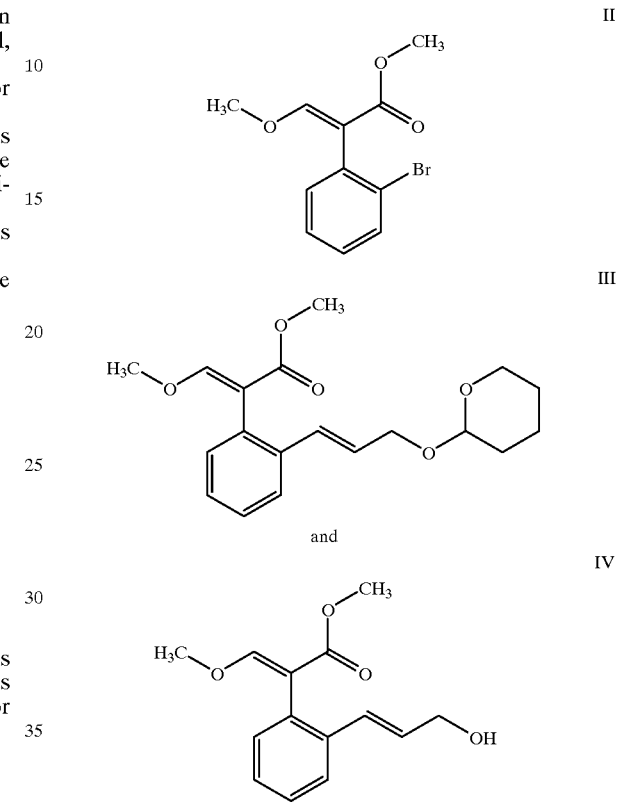

and

The compounds of formulae IA and IB can be prepared as described in the documents cited above.

In addition, compounds of formulas IA1–IA9 and IB 1-IB5, can be prepared in accordance with Schemes 1–14.

Scheme 1

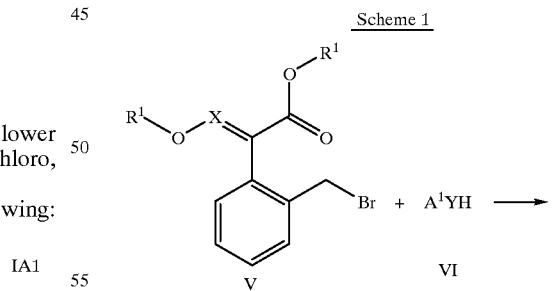

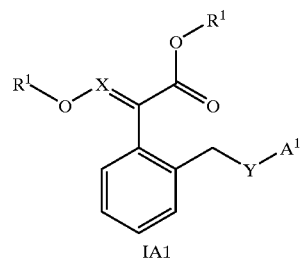

IA1 wherein the substituents have the significances described above.
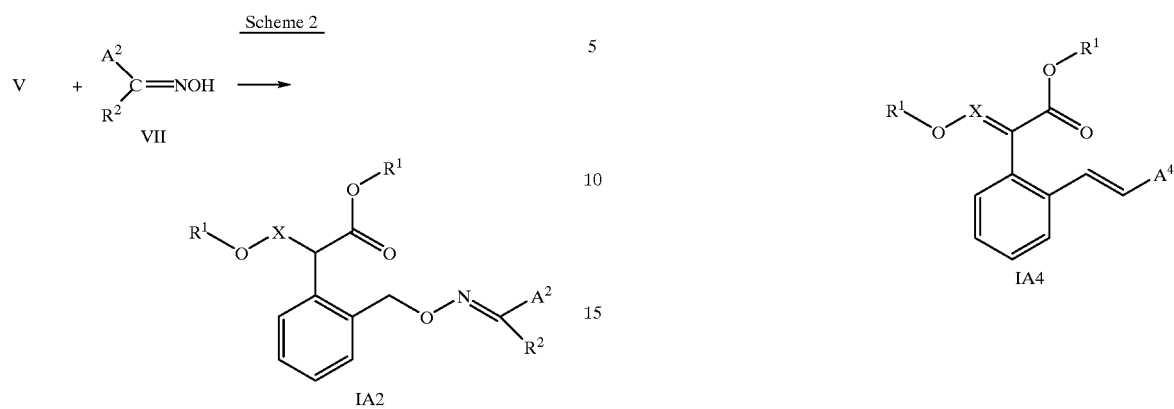
wherein the substituents have the significances described above.
wherein the substituents have the significances described above.
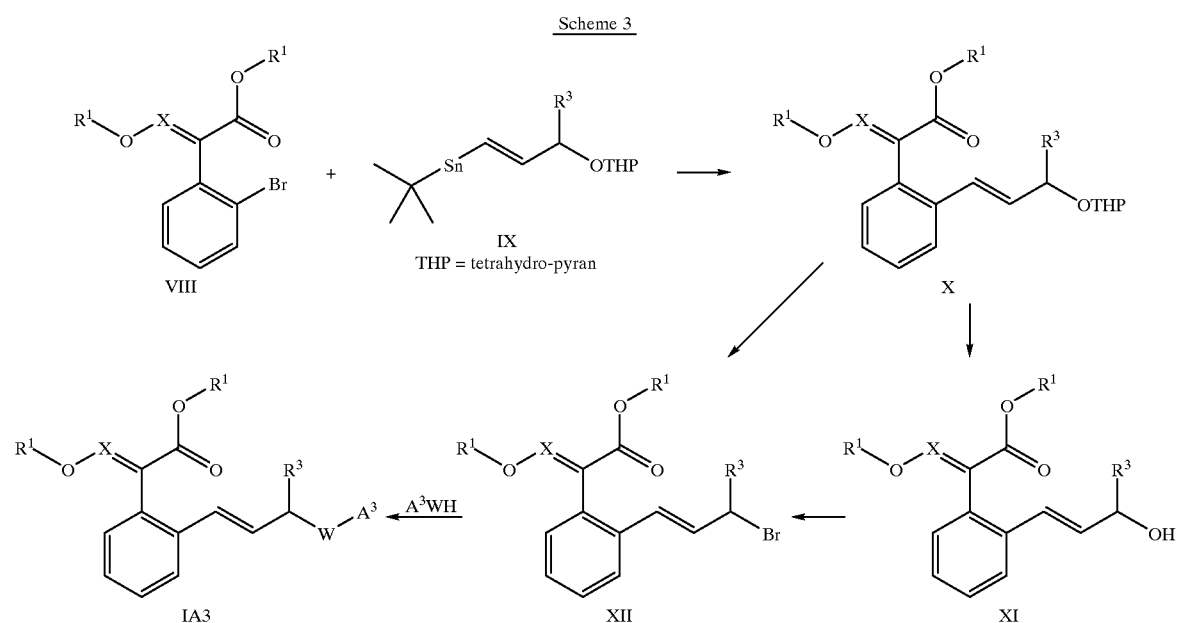
wherein the substituents have the significances described above.
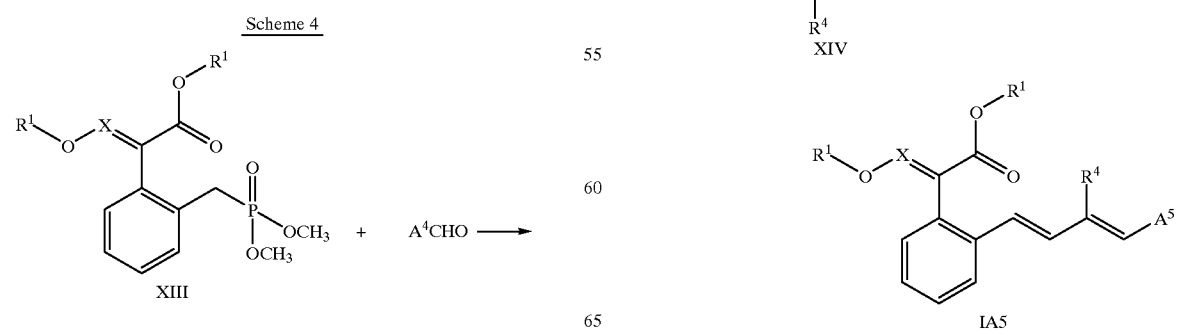

wherein the substituents have the significances described above.

Scheme 6

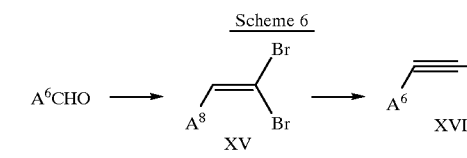

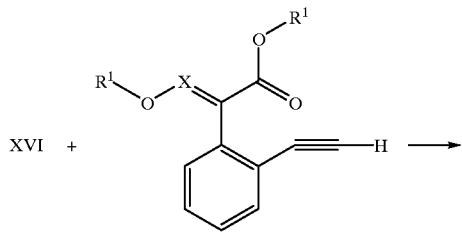

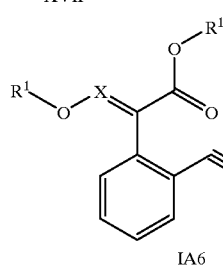

wherein the substituents have the significances described above.

Scheme 7

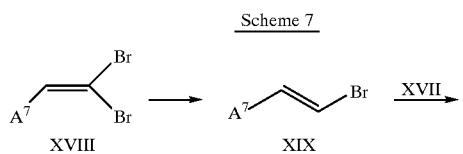

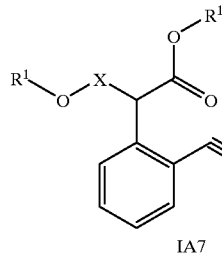

wherein the substituents have the significances described above.

Scheme 8

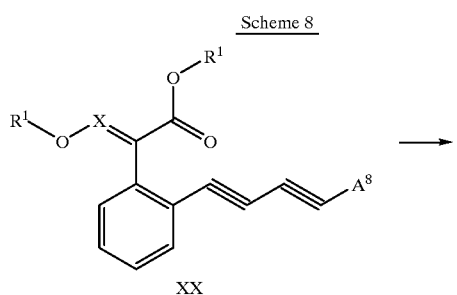

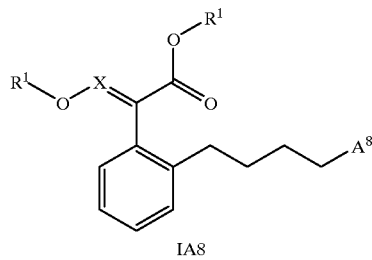

wherein the substituents have the significances described above.

Scheme 9

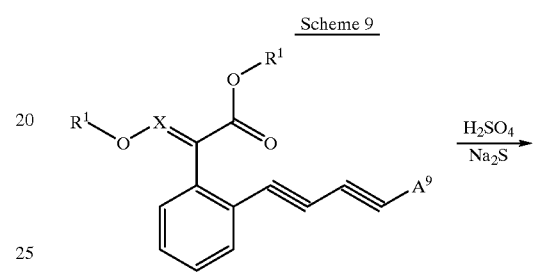

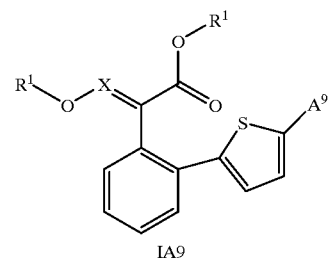

wherein the substituents have the significances described above.

Scheme 10

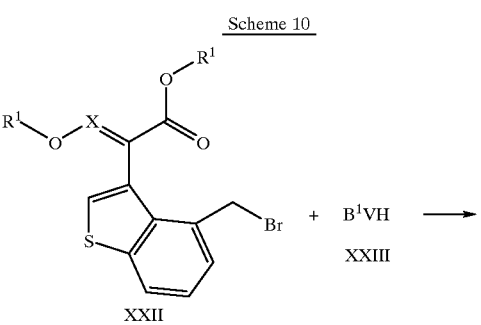

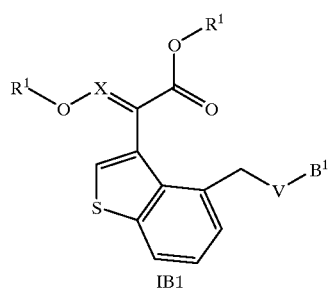

wherein the substituents have the significances described above.

Scheme 11

XXII + 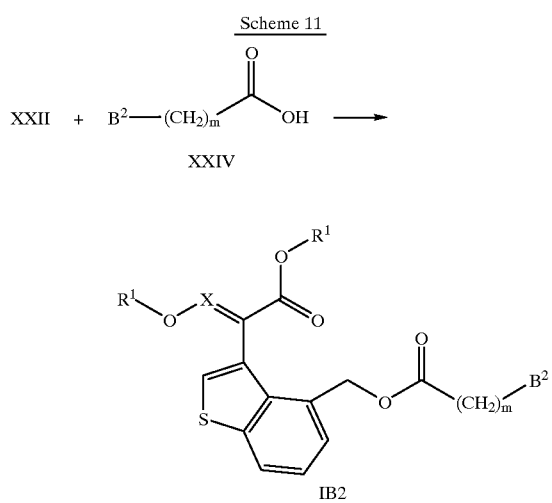

wherein the substituents have the significances described above.

Scheme 12

XXII + 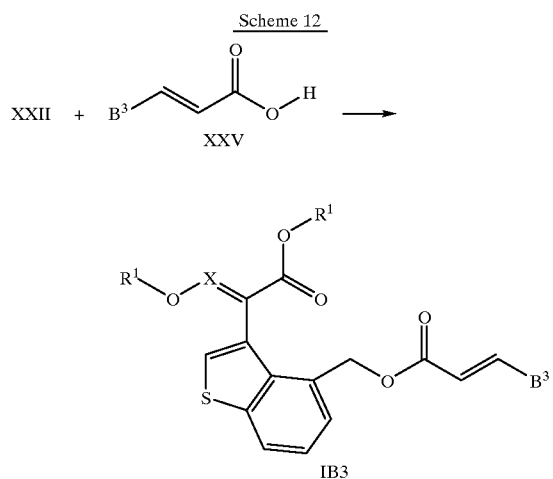

wherein the substituents have the significances described above.

Scheme 13

XXII + 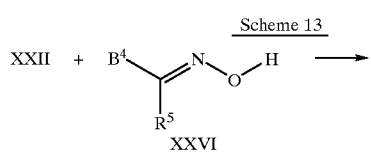

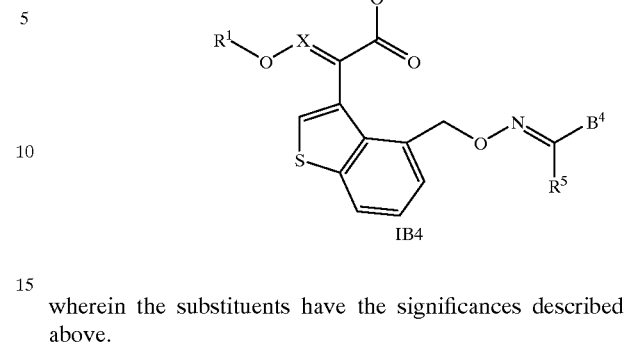

wherein the substituents have the significances described above.

Scheme 14

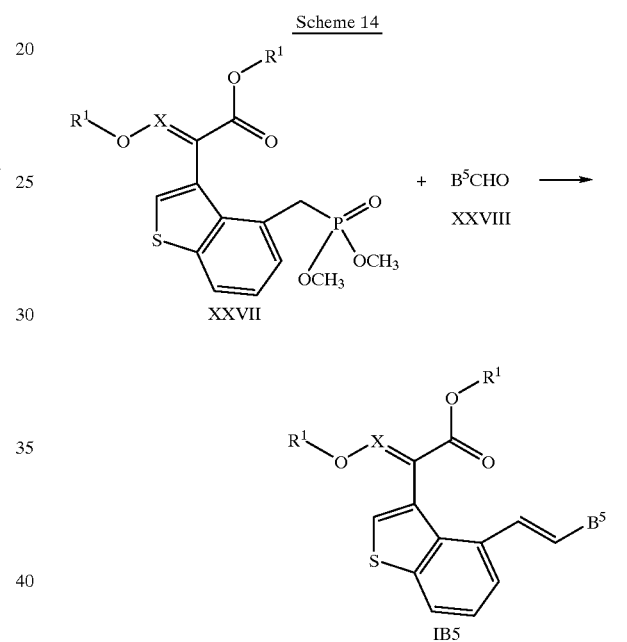

wherein the substituents have the significances described above.

The novel compounds of formula IA5 can be prepared in accordance with Scheme 5 and by Examples 164–206.

As mentioned earlier, the β-alkoxyacrylates of formulae IA and IB in accordance with the invention and their pharmaceutically usable salts have valuable pharmaceutical properties.

In particular, they have a very good activity against malaria pathogens. Their activity is equally good against chloroquine-resistant strains of the pathogen as against chloroquine-sensitive strains. Accordingly, the present compounds can also be used for the prophylaxis and cure of malaria even in those cases where the pathogen does not respond to chloroquine.

In the following table are described the tested compounds:

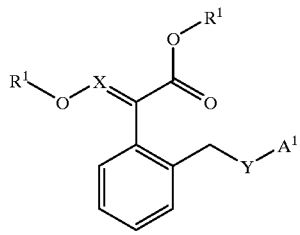
IA1
| R¹ | X | Y | A¹ | Expl.No. |
|---|---|---|---|---|
| CH₃ | —CH | S | 2,4,5-trichlorophenyl | 1 |
| CH₃ | CH | S | 4-fluorophenyl | 2 |
| CH₃ | —CH | S | 2,5-dichlorophenyl | 3 |
| CH₃ | —CH | S | 2-naphthyl | 4 |
| CH₃ | —CH | S | 2-chlorophenyl | 5 |
| CH₃ | —CH | S | 2-methoxyphenyl | 6 |
| CH₃ | CH | S | 2-isopropylphenyl | 7 |

-continued
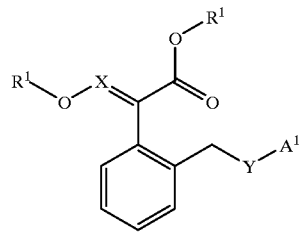
IA1
| R¹ | X | Y | A¹ | Expl.No. |
|---|---|---|---|---|
| CH₃ | —CH | S | 4-methyl-3-nitro-(trifluoromethyl)phenyl | 8 |
| CH₃ | CH | S | 4-bromophenyl-methyl | 9 |
| CH₃ | CH | S | 2,3-dimethylphenyl | 10 |
| CH₃ | CH | S | pentafluorophenyl-methyl | 11 |
| CH₃ | CH | S | 4-methoxyphenyl-methyl | 12 |
| CH₃ | CH | S | 1,4-dimethylphenyl | 13 |
| CH₃ | CH | S | 4-tert-butylphenyl-methyl | 14 |
| CH₃ | CH | S | 2-(trifluoromethyl)-methylphenyl | 15 |

-continued
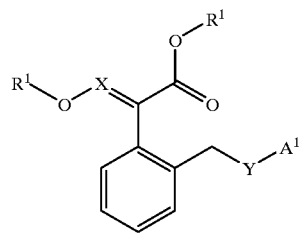
IA1
| $R^1$ | X | Y | $A^1$ | Expl.No. |
|---|---|---|---|---|
| $CH_3$ | CH | S |  | 16 |
| $CH_3$ | CH | S | 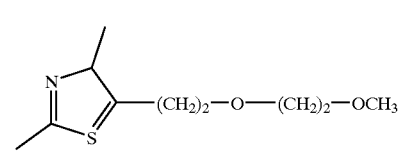 | 17 |
| $CH_3$ | CH | S | 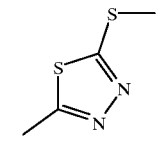 | 18 |
| $CH_3$ | CH | S | 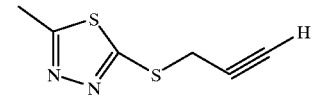 | 19 |
| $CH_3$ | CH | S | 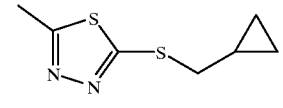 | 20 |
| $CH_3$ | CH | S | 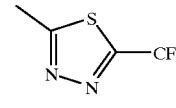 | 21 |
| $CH_3$ | CH | S | 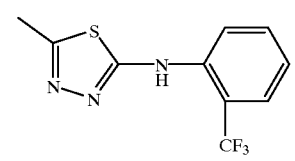 | 22 |
| $CH_3$ | CH | S | 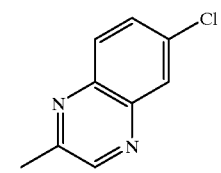 | 23 |

-continued
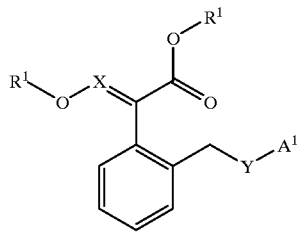
IA1
| R¹ | X | Y | A¹ | Expl.No. |
|---|---|---|---|---|
| CH₃ | CH | S | 2,4-dimethylthiazol-5-yl ethyl carboxylate | 24 |
| CH₃ | CH | S | 2-(2,4-dimethylthiazol-5-yl)ethyl acetate | 25 |
| CH₃ | CH | S | 2-benzoxazolyl | 26 |
| CH₃ | CH | O | 3-methyl-4-oxo-3,4-dihydro-1,2,3-benzotriazin-yl | 27 |
| CH₃ | CH | O | 7-bromo-3,5-dimethylquinoxalin-2-yl | 28 |
| CH₃ | CH | O | 7-bromo-3,5,6-trimethylquinoxalin-2-yl | 29 |
| CH₃ | CH | O | 2-methylquinolin-yl | 30 |
| CH₃ | CH | O | 3,8-dimethylquinoxalin-2-yl | 31 |

-continued

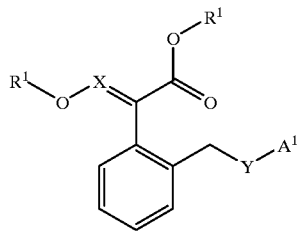

IA1

| R¹ | X | Y | A¹ | Expl.No. |
|---|---|---|---|---|
| CH₃ | CH | O | 3-methyl-quinoxalin-2-yl | 32 |
| CH₃ | CH | O | 3-methyl-isothiazol-5-yl | 33 |
| CH₃ | CH | O | 7-chloro-3-methyl-quinoxalin-2-yl | 34 |
| CH₃ | CH | O | 4-tert-butyl-2-methyl-phenyl | 35 |

Preferred compounds are also those of formula IA1 wherein $R^1$ is methyl, X is CH, Y is S or O, $A^1$ is phenyl which is substituted by one or more substituents selected from halogen, lower alkoxy, lower alkyl, $CF_3$, $NO_2$, $NH_2$, phenoxy, or $CF_3$-phenoxy. Such compounds can be prepared according to the procedure set in example 1 of EP 278595, like the following specific compounds:

(E)-2-[2-(2-Bromo-phenoxymethyl)-phenyl]-3-methoxy-acrylic acid methyl ester;

(E)-3-methoxy-2-[2-(4-phenoxy-phenoxymethyl)-phenyl]-acrylic acid methyl ester;

(E)-3-methoxy-2-[2-[4-(4-trifluoromethyl-phenoxy)-phenoxymethyl]-phenyl]-acrylic acid methyl ester;

(E)-3-methoxy-2-[2-(4-methoxy-2-nitro-phenoxymethyl)-phenyl]-acrylic acid methyl ester;

(E)-2-[2-(2,4-dibromo-phenoxymethyl)-phenyl]-3-methoxy-acrylic acid methyl ester;

(E)-2-[2-(2-chloro-4-methyl-phenoxymethyl)-phenyl]-3-methoxy-acrylic acid methyl ester;

(E)-2-[2-(2-chloro-4-trifluoromethyl-phenoxymethyl)-phenyl]-3-methoxy-acrylic acid methyl ester;

(E)-3-methoxy-2-(2-pentafluorophenyloxymethyl-phenyl)-acrylic acid methyl ester;

(E)-2-[2-(2,4-dichloro-phenylsulfanylmethyl)-phenyl]-3-methoxy-acrylic acid methyl ester;

(E)-2-[2-(2-amino-4-trifluoromethyl-phenylsulfanylmethyl)-phenyl]-3-methoxy-acrylic acid methyl ester;

(E)-2-[2-(2-amino-4-methoxy-phenoxymethyl)-phenyl]-3-methoxy-acrylic acid methyl ester; and (E)-2-[2-(4-tert-butyl-2-chloro-phenoxymethyl)-phenyl]-3-methoxy-acrylic acid methyl ester.

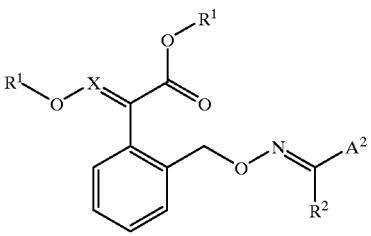

IA2

| R¹ | X | R² | A² | Expl. No. |
|---|---|---|---|---|
| CH₃ | CH | —C(O)OCH₃ | 2-methylphenyl | 36 |

-continued

IA2

| R¹ | X | R² | A² | Expl. No. |
|---|---|---|---|---|
| CH₃ | CH | CF₃ | 3-(CF₃)C₆H₄- | 37 |
| CH₃ | CH | CH₃ | 3,5-Cl₂C₆H₃- | 38 |
| CH₃ | CH | —(CH₂)₂CH₃ | 3-(CF₃)C₆H₄- | 39 |
| CH₃ | CH | cyclopropyl | 3-(CF₃)C₆H₄- | 40 |
| CH₃ | CH | cyclopropyl | 2-pyridyl | 41 |
| CH₃ | CH | —CH₂OCH₃ | 2-pyridyl | 42 |
| CH₃ | CH | CH₃ | 2-CF₃-4-Cl-C₆H₃- | 43 |
| CH₃ | CH | CH₃ | 4-(CF₃)-2-(SCH₃)C₆H₃- | 44 |
| CH₃ | CH | H | 4-tert-butyl-C₆H₄-C(CH₃)=CH- | 45 |
| CH₃ | CH | CH₂CH₃ | 3-pyridyl | 46 |
| CH₃ | CH | CH₃ | 2-(CF₃)C₆H₄- | 47 |
| CH₃ | CH | CH₃ | 3-(OCH₃)C₆H₄- | 48 |
| CH₃ | CH | CH₃CH₃ | 3-Cl-C₆H₄- | 49 |
| CH₃ | CH | CH₂CH₃ | 4-F-C₆H₄- | 50 |
| CH₃ | CH | CH₂CH₃ | 4-Br-C₆H₄- | 51 |
| CH₃ | CH | CH₃ | 4-tert-butyl-C₆H₄- | 52 |

-continued
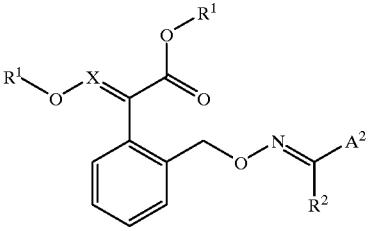
| R¹ | X | R² | A² | Expl. No. |
|---|---|---|---|---|
| CH₃ | CH | CH₃ | 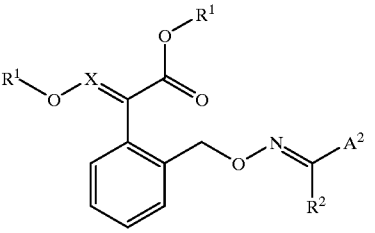 | 53 |
| CH₃ | CH | CH₃ | 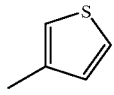 | 54 |
| CH₃ | CH | CH₃ | 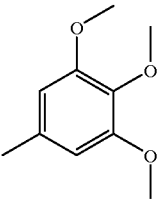 | 55 |
| CH₃ | CH | CH₃ | 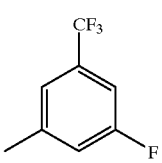 | 56 |
| CH₃ | CH | CH₂CH₃ | 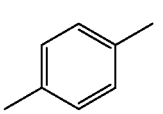 | 57 |
| CH₃ | CH | CH₂CH₃ | 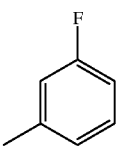 | 58 |
| CH₃ | CH | CH₂CH₃ | 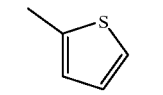 | 59 |
| CH₃ | CH | CH₂SCH₃ | 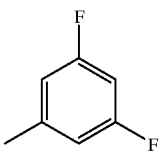 | 60 |
-continued
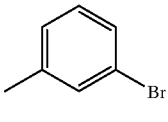
| R¹ | X | R² | A² | Expl. No. |
|---|---|---|---|---|
| CH₃ | CH | CH₃ | 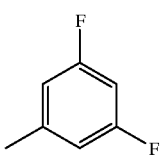 | 61 |
| CH₃ | CH | H | 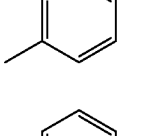 | 62 |
| CH₃ | CH | H | 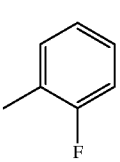 | 63 |
| CH₃ | CH | H | 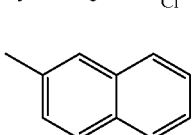 | 64 |
| CH₃ | CH | H | 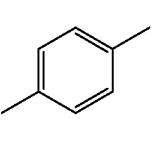 | 65 |
| CH₃ | CH | H | 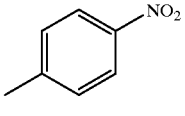 | 66 |
| CH₃ | CH | CH₂CH₃ | 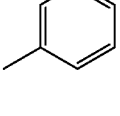 | 67 |
| CH₃ | CH | H | 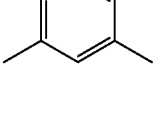 | 68 |
| CH₃ | CH | CH₃ | 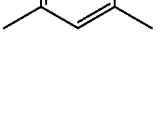 | 69 |

-continued
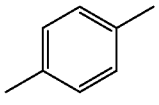
IA2
| R¹ | X | R² | A² | Expl. No. |
|---|---|---|---|---|
| CH₃ | CH | CH₃ | 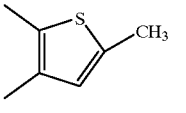 | 70 |
| CH₃ | CH | H | 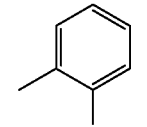 | 71 |
| CH₃ | CH | H | 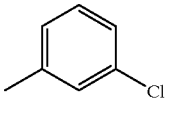 | 72 |
| CH₃ | CH | CH₃ | 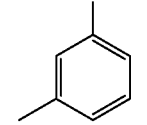 | 73 |
| CH₃ | CH | CH₃ | 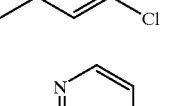 | 74 |
| CH₃ | CH | CH₃ | 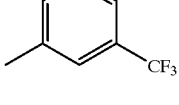 | 75 |
| CH₃ | CH | CH₃ | 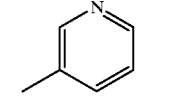 | 76 |
| CH₃ | CH | CH₃ | 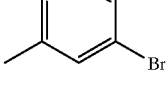 | 77 |
| CH₃ | CH | CH₃ | 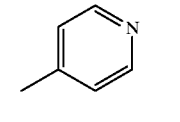 | 78 |
| CH₃ | CH | CH₃ | 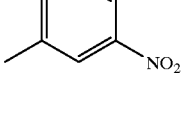 | 79 |
| CH₃ | CH | CH₃ | 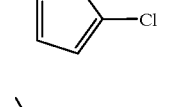 | 80 |
| CH₃ | CH | CH₃ | 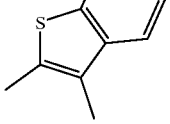 | 81 |
| CH₃ | CH | CH₃ | 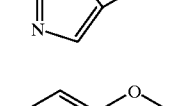 | 82 |
| CH₃ | CH | CH₃ | 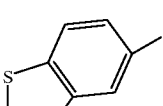 | 83 |
| CH₃ | CH | CH₃ | 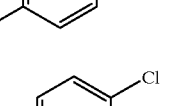 | 84 |
| CH₃ | CH | CH₃ | 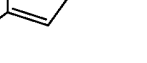 | 85 |
| CH₃ | CH | CH₃ | 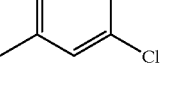 | 86 |
| CH₃ | CH | H |  | 87 |

-continued

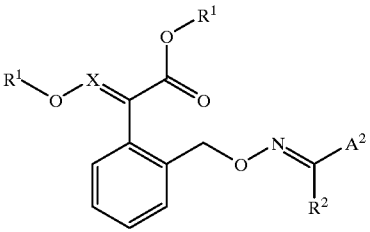

IA2

| R¹ | X | R² | A² | Expl. No. |
|---|---|---|---|---|
| CH₃ | CH | CH₃ | 2-thienyl | 88 |
| CH₃ | CH | CH₃ | 4-chlorophenyl | 89 |
| CH₃ | CH | CH₂CH₃ | 4-chlorophenyl | 90 |
| CH₃ | CH | (CH₂)₂CH₃ | phenyl | 91 |
| CH₃ | CH | cyclopropyl | phenyl | 92 |
| CH₃ | CH | CH₃ | benzoyl | 93 |
| CH₃ | CH | CH₃ | styryl (CH=CH-Ph) | 94 |
| CH₃ | CH | H | 4-(CF₃)phenyl | 95 |
| CH₃ | CH | CF₃ | phenyl | 96 |
| CH₃ | CH | CH₃ | 4-NO₂-phenyl | 97 |

-continued

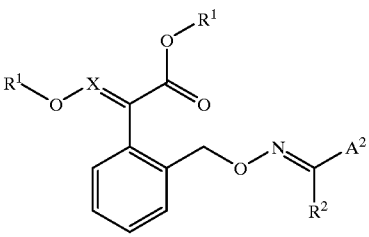

IA2

| R¹ | X | R² | A² | Expl. No. |
|---|---|---|---|---|
| CH₃ | CH | H | phenyl | 98 |
| CH₃ | CH | H | 2-pyridyl | 99 |
| CH₃ | CH | H | 4-pyridyl | 100 |
| CH₃ | CH | CH₃ | 2-benzofuryl | 101 |
| CH₃ | CH | H | 2,4-dichlorophenyl | 102 |
| CH₃ | CH | H | 2-quinolyl | 103 |
| CH₃ | CH | CH₃ | phenyl | 104 |
| CH₃ | CH | CH₃ | 3,5-bis(CF₃)phenyl | 105 |
| CH₃ | CH | CH₃ | 4-fluoro-2-methylphenyl | 106 |

-continued

IA2

[Structure: phenyl ring with ortho substituents — one bearing =X-O-R¹ and C(=O)-O-R¹ (methyl (E)-methoxyimino acetate type), the other bearing -CH₂-O-N=C(R²)(A²)]

| R¹ | X | R² | A² | Expl. No. |
|---|---|---|---|---|
| CH₃ | CH | CH₃ | 3,4-difluorophenyl | 107 |
| CH₃ | CH | CH₃ | 2,5-difluorophenyl | 108 |
| CH₃ | CH | CH₃ | 2,4-difluorophenyl | 109 |
| CH₃ | N | CH₃ | 3-(trifluoromethyl)phenyl | 110 |
| CH₃ | N | CH₃ | 3,5-bis(trifluoromethyl)phenyl | 111 |
| CH₃ | N | CF₃ | phenyl | 112 |
| CH₃ | N | CH₃ | 4-nitrophenyl | 113 |
| CH₃ | N | CH₃ | 3-bromophenyl | 114 |

-continued

IA2

[Same IA2 structure]

| R¹ | X | R² | A² | Expl. No. |
|---|---|---|---|---|
| CH₃ | N | CH₃ | 4-methoxyphenyl | 115 |
| CH₃ | CH | CH₃ | 4-chlorophenyl | 116 |
| CH₃ | CH | CH₃ | 3,4-dichlorophenyl | 117 |

IA3

[Structure: phenyl ring with ortho substituents — one bearing =X-O-R¹ and C(=O)-O-R¹, the other bearing -CH=CH-C(R³)(W-A³)]

| R¹ | X | R³ | W | A³ | Expl. No. |
|---|---|---|---|---|---|
| CH₃ | CH | H₂ | S | pentafluorophenyl | 118 |
| CH₃ | CH | H₂ | S | 4-tert-butylphenyl | 119 |

-continued

IA3

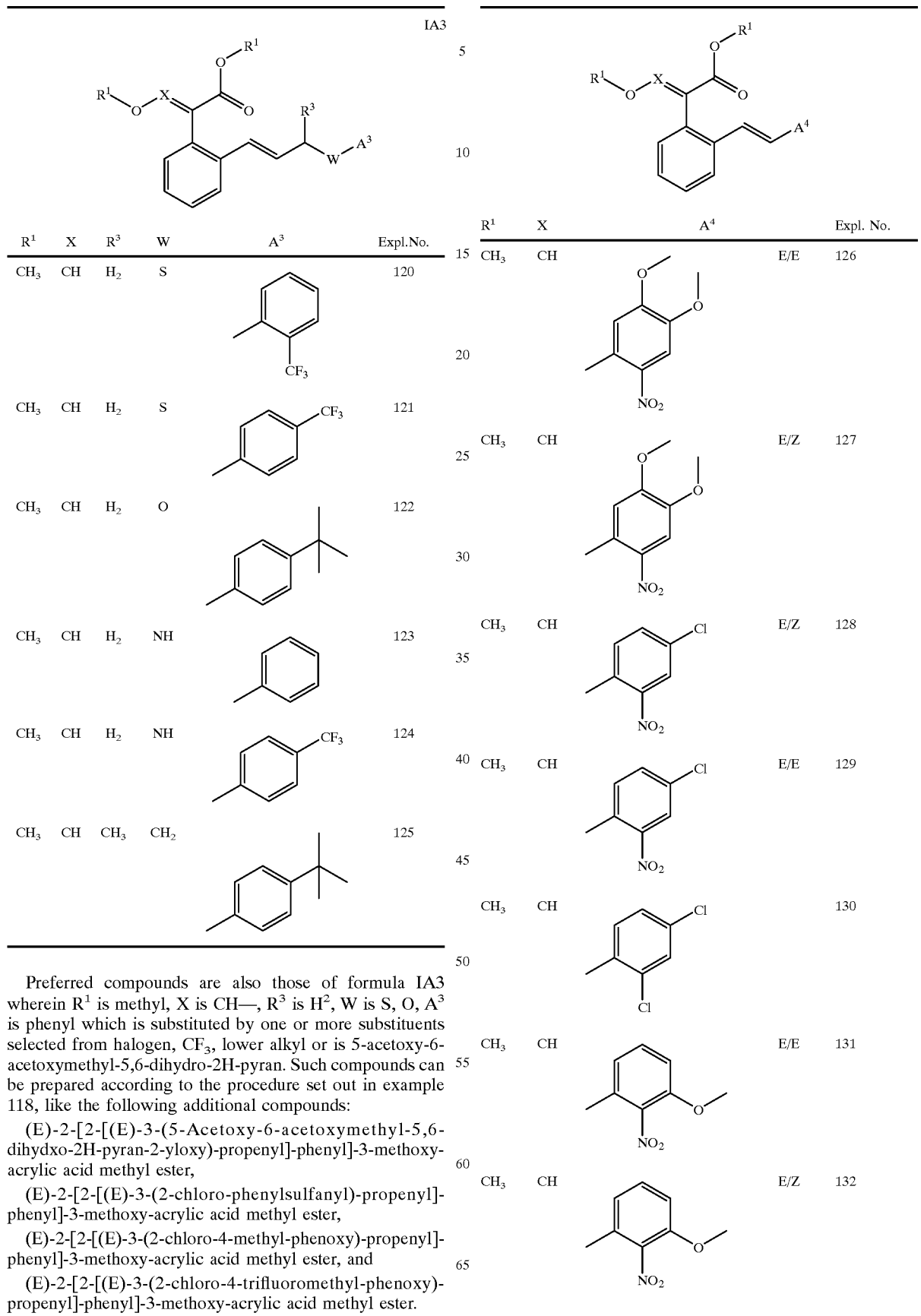

| R¹ | X | R³ | W | A³ | Expl.No. |
|---|---|---|---|---|---|
| CH₃ | CH | H₂ | S | 2-CF₃-phenyl | 120 |
| CH₃ | CH | H₂ | S | 4-CF₃-phenyl | 121 |
| CH₃ | CH | H₂ | O | 4-tert-butyl-phenyl | 122 |
| CH₃ | CH | H₂ | NH | phenyl | 123 |
| CH₃ | CH | H₂ | NH | 4-CF₃-phenyl | 124 |
| CH₃ | CH | CH₃ | CH₂ | 4-tert-butyl-phenyl | 125 |

Preferred compounds are also those of formula IA3 wherein R¹ is methyl, X is CH—, R³ is H², W is S, O, A³ is phenyl which is substituted by one or more substituents selected from halogen, CF₃, lower alkyl or is 5-acetoxy-6-acetoxymethyl-5,6-dihydro-2H-pyran. Such compounds can be prepared according to the procedure set out in example 118, like the following additional compounds:

(E)-2-[2-[(E)-3-(5-Acetoxy-6-acetoxymethyl-5,6-dihydxo-2H-pyran-2-yloxy)-propenyl]-phenyl]-3-methoxy-acrylic acid methyl ester, (E)-2-[2-[(E)-3-(2-chloro-phenylsulfanyl)-propenyl]-phenyl]-3-methoxy-acrylic acid methyl ester, (E)-2-[2-[(E)-3-(2-chloro-4-methyl-phenoxy)-propenyl]-phenyl]-3-methoxy-acrylic acid methyl ester, and (E)-2-[2-[(E)-3-(2-chloro-4-trifluoromethyl-phenoxy)-propenyl]-phenyl]-3-methoxy-acrylic acid methyl ester.

| R¹ | X | A⁴ | | Expl. No. |
|---|---|---|---|---|
| CH₃ | CH | 4,5-dimethoxy-2-nitro-phenyl | E/E | 126 |
| CH₃ | CH | 4,5-dimethoxy-2-nitro-phenyl | E/Z | 127 |
| CH₃ | CH | 4-chloro-2-nitro-phenyl | E/Z | 128 |
| CH₃ | CH | 4-chloro-2-nitro-phenyl | E/E | 129 |
| CH₃ | CH | 2,4-dichloro-phenyl | | 130 |
| CH₃ | CH | 2-methoxy-3-nitro-phenyl | E/E | 131 |
| CH₃ | CH | 2-methoxy-3-nitro-phenyl | E/Z | 132 |

-continued
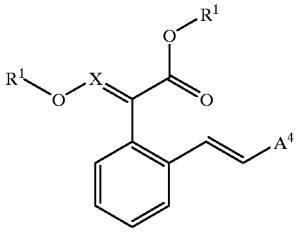
| R¹ | X | A⁴ | Expl. No. |
|---|---|---|---|
| CH₃ | CH | 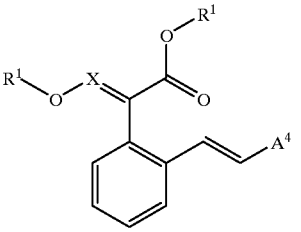 | 133 |
| CH₃ | CH | 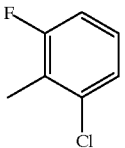 | 134 |
| CH₃ | CH | 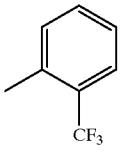 | 135 |
| CH₃ | CH | 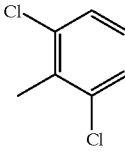 | 136 |
| CH₃ | CH | 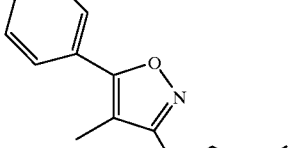 | 137 |
| CH₃ | CH | 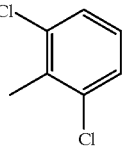 | 138 |
| CH₃ | CH | 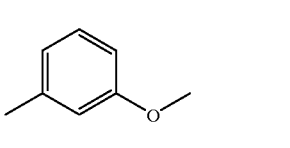 | 139 |
-continued
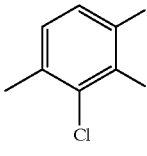
| R¹ | X | A⁴ | | Expl. No. |
|---|---|---|---|---|
| CH₃ | CH | 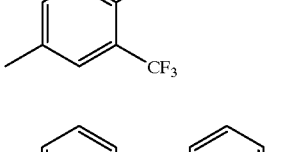 | | 140 |
| CH₃ | CH | 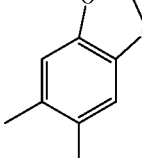 | | 141 |
| CH₃ | CH | 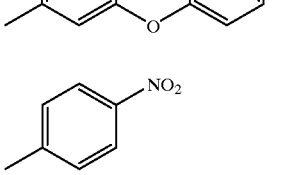 | | 142 |
| CH₃ | CH | 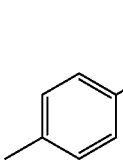 | | 143 |
| CH₃ | CH | 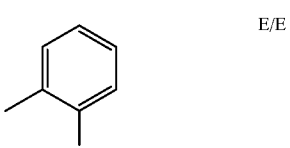 | | 144 |
| CH₃ | CH | 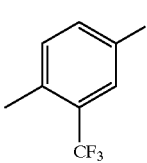 | | 145 |
| CH₃ | CH | 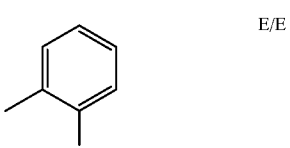 | E/E | 146 |
| CH₃ | CH | 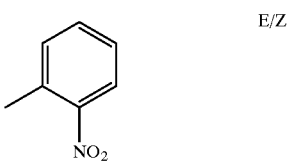 | E/Z | 147 |

-continued

| R¹ | X | A⁴ | Expl. No. |
|---|---|---|---|
| CH₃ | CH | 3-CF₃-phenyl | 148 |
| CH₃ | CH | benzo[1,3]dioxol-5-yl | 149 |
| CH₃ | CH | quinolin-3-yl | 150 |
| CH₃ | CH | pyridin-4-yl | 151 |
| CH₃ | CH | pyridin-3-yl | 152 |
| CH₃ | CH | pyridin-2-yl | 153 |
| CH₃ | CH | furan-2-yl | 154 |
| CH₃ | CH | thiophen-2-yl | 155 |
| CH₃ | CH | -C≡C-C(CH₃)₃ | 156 |
| CH₃ | CH | phenyl | 157 |

-continued

| R¹ | X | A⁴ | Expl. No. |
|---|---|---|---|
| CH₃ | CH | indolizin-yl | 158 |
| CH₃ | CH | thiophen-2-yl (Me-substituted) | 159 |
| CH₃ | CH | benzofuran-2-yl | 160 |
| CH₃ | CH | methyl-dihydrobenzothiophene | 161 |
| CH₃ | CH | -C≡C-phenyl | 162 |
| CH₃ | CH | methyl-2H-chromenyl | 163 |

Preferred compounds are also those of formula IA4 wherein R¹ is methyl, X is CH, and A⁴ is phenyl which is substituted by one or more substituents selected from halogen, lower alkoxy, NO₂, styryl-phenyl, or (2-CF₃—, or Cl-phenyl)-furan-2-yl. Such compounds can be prepared according to the procedure set in example 126 (EP-475158 A2 920318), like:

(E)-3-Methoxy-2-[2-[(E)-2-[5-(2-trifluoromethyl-phenyl)-furan-2-yl]-vinyl]-phenyl]-acrylic acid methyl ester, (E)-2-[2-[(E)-2-(2-chloro-3,4-dimethoxy-6-nitro-phenyl)-vinyl]-phenyl]-3-methoxy-acrylic acid methyl ester, (E)-2-[2-[(E)-2-[5-(2-chloro-phenyl)-furan-2-yl]-vinyl]-phenyl]-3-methoxy-acrylic acid methyl ester and (E)-3-methoxy-2-[2-[(E)-2-[(E)-4-styryl-phenyl]-vinyl]-phenyl]-acrylic acid methyl ester.

-continued

| R¹ | R⁴ | A⁵ | X | Expl. No. |
|---|---|---|---|---|
| CH₃ | H | 4-methylpyridin-yl | CH | 164 |
| CH₃ | H | 4,5-dimethoxy-2-nitro-phenyl (methyl-substituted) | CH | 164 |
| CH₃ | H | 2,4-dichlorophenyl (methyl-substituted) | CH | 165 |
| CH₃ | H | 2-methylpyridin-yl | CH | 166 |
| CH₃ | H | 2,3-dichlorophenyl (methyl-substituted) | CH | 167 |
| CH₃ | H | 2,3-difluorophenyl (methyl-substituted) | CH | 168 |
| CH₃ | H | 2-methylquinolinyl | CH | 169 |
| CH₃ | H | 1-methylnaphthyl | CH | 170 |
| CH₃ | H | 1,2-dimethylpyrrolyl | CH | 171 |
| CH₃ | H | 4-methylpyridinyl | CH | 172 |
| CH₃ | H | 2-methylfuryl | CH | 173 |
| CH₃ | H | 2-methylthienyl | CH | 174 |
| CH₃ | H | 3-methylthienyl | CH | 175 |
| CH₃ | H | 4-methylisoquinolinyl | CH | 176 |
| CH₃ | H | 4-(trifluoromethyl)phenyl (methyl-substituted) | CH | 177 |
| CH₃ | H | 4-fluorophenyl (methyl-substituted) | CH | 178 |
| CH₃ | H | 2-ethoxyphenyl (methyl-substituted) | CH | 179 |
| CH₃ | H | 3-chloro-6-fluorophenyl (methyl-substituted) | CH | 180 |

-continued

| R¹ | R⁴ | A⁵ | X | Expl. No. |
|---|---|---|---|---|
| CH₃ | H | 3-(CF₃)-phenyl | CH | 181 |
| CH₃ | H | furan-3-yl | CH | 182 |
| CH₃ | H | 2-(4-chlorophenyl)-4-methylthiazol-5-yl | CH | 183 |
| CH₃ | H | 2-chlorophenyl | CH | 184 |
| CH₃ | H | 2-(CF₃)-phenyl | CH | 185 |
| CH₃ | H | 3-fluorophenyl | CH | 186 |
| CH₃ | H | 4-methyl-5-phenylthiazol-2-yl | CH | 187 |
| CH₃ | H | 5-bromothiophen-2-yl | CH | 188 |
| CH₃ | H | 4-methoxyphenyl | CH | 189 |

-continued

| R¹ | R⁴ | A⁵ | X | Expl. No. |
|---|---|---|---|---|
| CH₃ | H | 3-methylbenzothiophen-2-yl | CH | 190 |
| CH₃ | H | thiazol-2-yl | CH | 191 |
| CH₃ | H | 5-methylthiophen-2-yl | CH | 192 |
| CH₃ | H | 3-methylthiophen-2-yl | CH | 193 |
| CH₃ | H | naphthalen-2-yl | CH | 194 |
| CH₃ | H | benzothiophen-2-yl | CH | 195 |
| CH₃ | H | benzothiophen-3-yl | CH | 196 |
| CH₃ | H | phenyl | CH | 197 |
| CH₃ | H | 3,5-bis(CF₃)-phenyl | CH | 198 |

-continued

| R¹ | R⁴ | A⁵ | X | Expl. No. |
|---|---|---|---|---|
| CH₃ | H | 2-methyl-4,5-bis(CF₃)-phenyl | CH | 199 |
| CH₃ | H | 4-chloro-2-methyl-phenyl | CH | 201 |
| CH₃ | H | 3-chloro-5-methyl-phenyl | CH | 202 |
| CH₃ | H | 2-bromo-6-methyl-phenyl | CH | 203 |
| CH₃ | H | 3,4,5-trimethoxy-phenyl (methyl-substituted) | CH | 204 |
| CH₃ | H | 4-tert-butyl-2-methyl-phenyl | CH | 205 |
| CH₃ | H | 2-CF₃-6-methyl-phenyl | CH | 206 |

Preferred compounds are also those of formula IA5 wherein R¹ is methyl, X is CH, R⁴ is H and A⁵ is phenyl, which is substituted by one or more substituents selected from lower alkyl, lower alkoxy, NO₂, halogen, cyano, or CF₃. Such compounds can be prepared according to the procedure set out in example 164, like:

(E)-2-[2-[(1E,3E)-4-(2-Chloro-3,4-dimethoxy-phenyl)-buta-1,3-dienyl]-phenyl]-3-methoxy-acrylic acid methyl ester, (E)-2-[2-[(1E,3E)-4-(2-bromo-4,5-dimethoxy-phenyl)-buta-1,3-dienyl]-phenyl]-3-methoxy-acrylic acid methyl ester, (E)-2-[2-[(1E,3E)-4-(2-cyano-phenyl)-buta-1,3-dienyl]-phenyl]-3-methoxy-acrylic acid methyl ester, (E)-3-methoxy-2-[2-[(1E,3E)-4-(3-methoxy-2-nitro-phenyl)-buta-1,3-dienyl]-phenyl]-acrylic acid methyl ester, (E)-2-[2-[(1E,3E)-4-(4-fluoro-2-trifluoromethyl-phenyl)-buta-1,3-dienyl]-phenyl]-acrylic acid methyl ester, (E)-2-[2-[(1E,3E)-4-(4-fluoro-2-trifluoromethyl-phenyl)-buta-1,3-dienyl]-phenyl]-3-methoxy-acrylic acid methyl ester, (E)-2-[2-[(1E,3E)-4-(4-tert-butyl-phenyl)-buta-1,3-dienyl]-phenyl]-3-methoxy-acrylic acid methyl ester, (E)-2-[2-[(1E,3E)-4-(2-chloro-4-fluoro-phenyl)-buta-1,3-dienyl]-phenyl]-3-methoxy-acrylic acid methyl ester, (E)-2-[2-[(1E,3E)-4-(2,4-difluoro-phenyl)-buta-1,3-dienyl]-phenyl]-3-methoxy-acrylic acid methyl ester, (E)-2-[2-[(1E,3E)-4-(2-chloro-4-methyl-phenyl)-buta-1,3-dienyl]-phenyl]-3-methoxy-acrylic acid methyl ester, (E)-2-[2-[(1E,3E)-4-(2,4-dimethyl-phenyl)-buta-1,3-dienyl]-phenyl]-3-methoxy-acrylic acid methyl ester and (E)-2-[2-[(1E,3E)-4-(2-fluoro-4-trifluoromethyl-phenyl)-buta-1,3-dienyl]-phenyl]-3-methoxy-acrylic acid methyl ester.

IA6

| R¹ | X | A⁶ | Expl. No. |
|---|---|---|---|
| CH₃ | N | 2-CF₃-phenyl | 207 |
| CH₃ | N | 2-methyl-4,5-bis(CF₃)-phenyl | 208 |

IA7

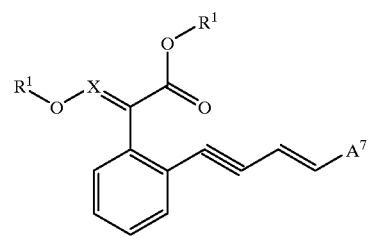

-continued
| $R^1$ | X | $A^7$ | Expl.No. |
|---|---|---|---|
| $CH_3$ | N | 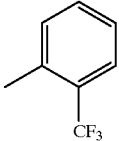 | 209 |
IA8
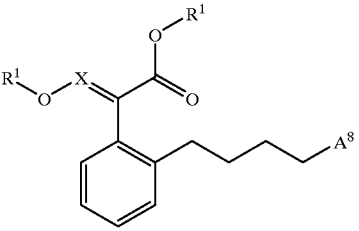
| $R^1$ | X | $A^8$ | Expl.No |
|---|---|---|---|
| $CH_3$ | CH | 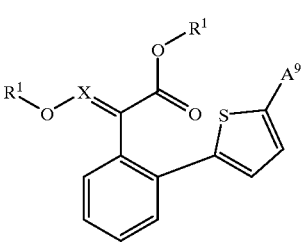 | 210 |
| $CH_3$ | CH | 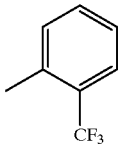 | 211 |
| $CH_3$ | CH | 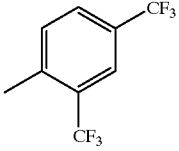 | 212 |
| $CH_3$ | CH | 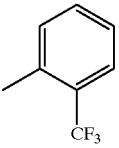 | 213 |
| $CH_3$ | CH | 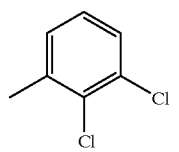 | 214 |
| $CH_3$ | N | 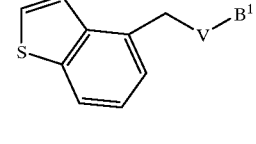 | 215 |
-continued
| | | | |
|---|---|---|---|
| $CH_3$ | N | 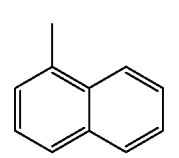 | 216 |
IA9
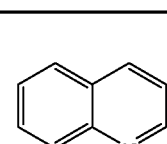
| $R^1$ | X | $A^9$ | Expl.No |
|---|---|---|---|
| $CH_3$ | B | 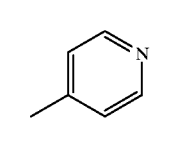 | 217 |
IB1
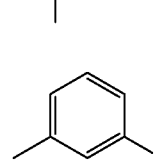
| $R^1$ | V | $B^1$ | X | Expl.No |
|---|---|---|---|---|
| $CH_3$ | —O— | 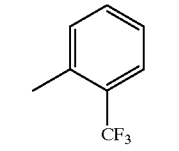 | CH | 218 |
| $CH_3$ | —O— | 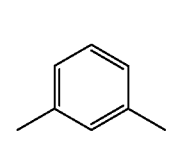 | CH | 219 |
| $CH_3$ | —N($CH_3$)— | 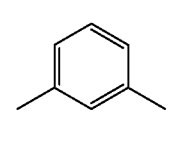 | CH | 220 |

-continued
| | | | | |
|---|---|---|---|---|
| CH₃ | —N(CH₃)— | 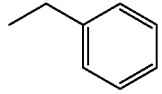 | CH | 221 |
| CH₃ | —N(CH₃)— | 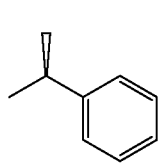 | CH | 222 |
| CH₃ | —N(CH₃)— | 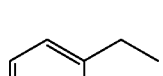 | CH | 223 |
| CH₃ | —S— | 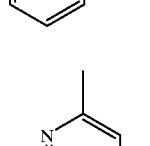 | CH | 224 |
IB2
| R¹ | B² | X | m | Expl.No. |
|---|---|---|---|---|
| CH₃ |  (4-Cl-phenyl) | CH | 1 | 225 |
| CH₃ | (2-F-phenyl) | CH | 0 | 226 |
| CH₃ | (phenyl) | CH | 0 | 227 |
| CH₃ | (2-Cl-phenyl) | CH | 1 | 228 |
-continued
| R¹ | B² | X | m | Expl.No. |
|---|---|---|---|---|
| CH₃ | (2-methylphenyl) | CH | 1 | 229 |
| CH₃ | (tolyl) | CH | 1 | 230 |
| CH₃ | (3,4-diCl-phenyl) | CH | 1 | 231 |
| CH₃ | (benzothienyl) | CH | 1 | 232 |
| CH₃ | (2,4-diCl-phenyl) | CH | 1 | 233 |
| CH₃ | (2,4-diCl-phenyl) | CH | 0 | 234 |
| CH₃ | (4-CF₃-phenyl) | CH | 1 | 235 |
IB3
| R¹ | B³ | X | Expl.No. |
|---|---|---|---|
| CH₃ | (3-CF₃-phenyl) | CH | 236 |

-continued

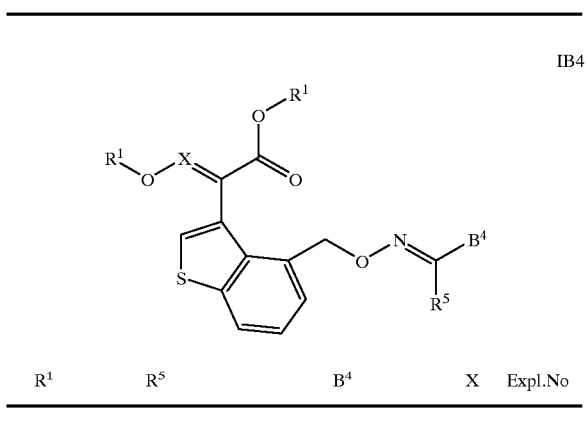

IB4

| $R^1$ | $R^5$ | $B^4$ | X | Expl.No |
|---|---|---|---|---|
| CH$_3$ | CH$_3$OCH$_2$CH$_2$— | 3-CF$_3$-C$_6$H$_4$ | CH | 237 |
| CH$_3$ | CH$_3$ | 3-CF$_3$-C$_6$H$_4$ | CH | 238 |
| CH$_3$ | CH$_3$ | 2-pyridyl | CH | 239 |
| CH$_3$ | H | 4,5-dimethyl-2-isopropyl-thiazoline | CH | 240 |

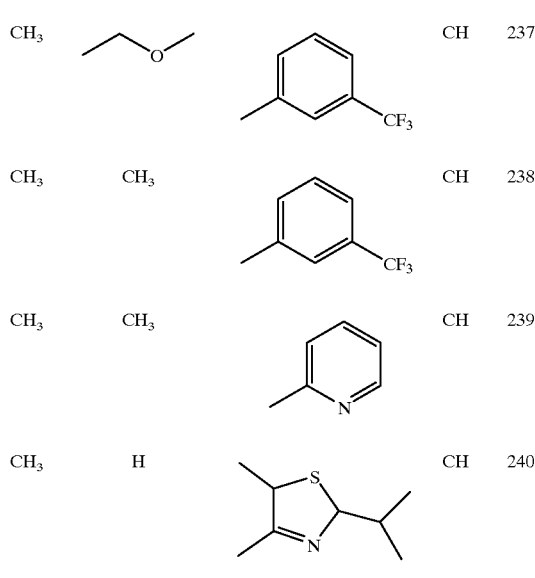

IB5

| $R^1$ | $B^5$ | X | Expl.No. |
|---|---|---|---|
| CH$_3$ | 4-methylphenyl | CH | 241 |
| CH$_3$ | 3,3-dimethyl-1-butynyl | CH | 242 |

-continued

| | | | | | |
|---|---|---|---|---|---|
| CH$_3$ | 3-methylthien-2-yl | | | CH | 243 |

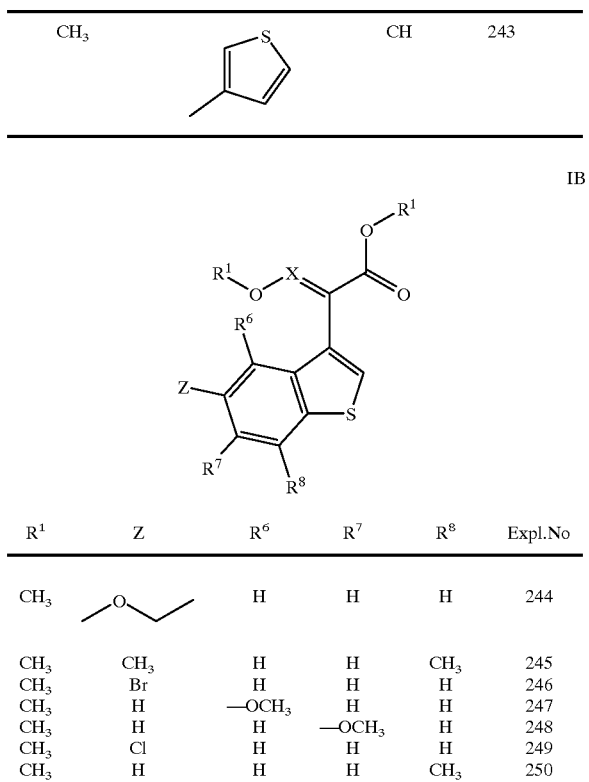

IB

| $R^1$ | Z | $R^6$ | $R^7$ | $R^8$ | Expl.No |
|---|---|---|---|---|---|
| CH$_3$ | OCH$_2$CH$_3$ | H | H | H | 244 |
| CH$_3$ | CH$_3$ | H | H | CH$_3$ | 245 |
| CH$_3$ | Br | H | H | H | 246 |
| CH$_3$ | H | —OCH$_3$ | H | H | 247 |
| CH$_3$ | H | H | —OCH$_3$ | H | 248 |
| CH$_3$ | Cl | H | H | H | 249 |
| CH$_3$ | H | H | H | CH$_3$ | 250 |

The activity of the compounds against not only chloroquine-resistant, but also chloroquine-sensitive malaria pathogens shows itself in a strong, in vitro measurable growth inhibition of various strains of the human-pathogenic *Plasmodium falciparum*, as set forth in Table 1 hereinafter. The ratio of the growth inhibition of a strain which is especially resistant to chloroquine and of a strain which is sensitive to chloroquine gives as the "resistance index" a measurement for the absence or presence of a cross-resistance with chloroquine. Since, for all novel compounds the resistance index lies between 0.7 and 2.5, they inhibit the growth of sensitive as well as resistant strains of the malaria pathogen equally effectively. They are accordingly also suitable for the prophylaxis of a malaria disease and also for the treatment of a malaria disease even when chloroquine is ineffective. The good activity against malaria pathogens is also shown in animal experiments. The effective doses measured after oral and subcutaneous administration to mice infected with malaria pathogens are shown in Table 2 hereinafter.

Test method for the determination of the activity against *Plasmodium falciparum* in vitro The preparations are tested on intraerythrocytary stages of *Plasmodium falciparum* from asynchronous cultures according to the method of Desjardin et al. (Desjardins, R. E. et al: Quantitative assessment of antimalarial activity in vitro by a semiautomated microdilution technique. Antimicrob. Agents Chemother. 16, 710–718, (1979)).

The culture medium consists of RPMI 1640 with the addition of 25 mM HEPES, 25 mM NaHCO$_3$, 100 μg/ml neomycin and 10% human serum (A$^+$). Human-A$^+$ erythrocytes are used as the *Plasmodium falciparum* host cells.

The parasites are maintained at 37° C. in an atmosphere of 3% $O_2$, 4% $CO_2$, 93% $N_2$ and 95% relative humidity.

In order to determine the activity, the preparations are dissolved in DMSO, pre-diluted in the culture medium to a suitable starting concentration and subsequently titrated-out on to microtitre plates in the 2nd stage over 6–7 steps. After the addition of the parasite culture (0.7% parasitemia in 2.5% erythrocyte suspension) the test plates are incubated under the conditions given above for 72 h. The parasite growth in the different preparation concentrations is determined using [G-$^3$H]-hypoxanthin incorporation compared to untreated control cultures on the same test plates. The 50% growth inhibition ($IC_{50}$) is calculated according to logit regression analysis from the resulting dosage-activity curve.

The preparations are tested on at least one chloroquine-resistant and one chloroquine-sensitive *Plasmodium falciparum* strain. Additional sensitive and resistant strains are included for further characterization.

Test method for the determination of the activity against *Plasmodium berghei* in vivo The preparations are tested on mice infected with malaria pathogens (*Plasmodium berghei*). Male albino mice (IBM:MORO(SPF), FUELLINSDORF) weighing about 25 g are used as the test animals. They are kept in climatized rooms at 21–22° C. in groups of 5 animals per cage. They receive ad libitum a diet feed with a low PABA content (NAFAG FUTTER" No. 9009 PAB-45, PABA content 45 mg/kg) and drinking water. On the first day of the test (D0) the test animals are infected with *Plasmodium berghei* (strain ANKA). For this there is used heparinized blood of a donor mouse with about 30% parasitemia, which is diluted with physiological saline such that it contains $10^8$ parasitized erythrocytes per ml. 0.2 ml of this suspension is injected intravenously (i.v.) into the mice to be treated and into the control mice. In untreated control animals the parasitemia normally reaches 30–40% on the third day after the infection (D+3) and the test animals die between days +5 and +7.

The substances to be tested are dissolved or suspended in distilled water or in a mixture of 7% Tween 80, 3% alcohol (96%) and water. Usually, 0.25 ml of this solution or suspension is administered once subcutaneously and perorally to groups of 5 test animals. Treatment is effected 24 hours after the infection. 10 control animals are treated in the same manner with solvent or suspension medium per test.

All substances are tested in a first test in a single dosage of 100 or 10 mg/kg. Only those substances which in this test (10 mg/kg) have shown a parasitaemia reduction of more than 90% are used for the titration. Suitable dilutions of the test substance can be used to obtain an accurate titration of the activity.

48 hours after the treatment (D+3) blood smears are prepared from all animals using blood from tail veins and are stained with giemsa. The average erythrocyte infection rate (parasitemiea in %) in the control groups as well as in the groups which have been treated with the test compounds is determined by counting under a microscope. The difference in the average values of the infection rates of control group (100%) and treated groups is calculated and expressed as a percentage reduction (GI%). The $ED_{50}$ or $ED_{90}$ is determined mathematically by means of the JMP programme (nonlinear fit). The $ED_{50}$ ($ED_{90}$) in mg/kg is that dose which after single administration reduces the average erythrocyte infection rate by 50% (90%) in comparison to the control group.

TABLE 1

Values measured in vitro ($IC_{50}$ values in μg/ml) for the grouth inhibition of the human-pathogenic *Plasmodium falciparum* strain NF54 as an example of a chloroquine-sensitive strain and of the human-pathogenic *Plasmodium flaciparum* K1 as an example of a chloroquine-resistant strain.

| | | in vitro | |
| --- | --- | --- | --- |
| Formula | Example No. | strain NF 54 $IC_{50}$ 72 h | strain K1 $IC_{50}$ 72 h |
| IA1 | 11 | 1.17 | 4.9 |
| IA1 | 28 | 17.7 | 19.1 |
| IA2 | 105 | 0.21 | 1.01 |
| IA2 | 110 | 20 | 65.8 |
| IA2 | 111 | 1.6 | 4.3 |
| IA3 | 120 | 1.75 | 2.51 |
| IA4 | 126 | 1.2 | 3.3 |
| IA4 | 136 | 1.04 | 2.9 |
| IA5 | 185 | 0.06 | 0.15 |
| IA5 | 199 | 0.06 | 0.13 |
| IA5 | 203 | 0.07 | 0.28 |
| IA5 | 206 | 0.4 | 1.4 |
| IA6 | 207 | 10.8 | 25.8 |
| IA7 | 209 | 3.21 | 5.7 |
| IA8 | 210 | 0.85 | 1.35 |
| IA8 | 211 | 0.33 | 1.34 |
| IA9 | 217 | 23.7 | 60.8 |
| IB1 | 222 | 22, 6 | 64.3 |
| 1B4 | 238 | 17.5 | 40.9 |
| IB5 | 241 | 1.4 | 7.4 |
| IB5 | 243 | 6.7 | 22.6 |
| IB | 244 | 147.3 | 419.2 |
| IB | 250 | 184.4 | 550.3 |
| IB2 | 233 | 29.5 | 67.3 |
| IB3 | 236 | 44.2 | 174.7 |
| III | 251 | 64.9 | 111 |

TABLE 2

Activity measured in vivo against *Plasmodium berghei* in mice in percentage reduction of the parasitemia after a perorally (po) or subcutaneously (sc) administered dose of 100 (10) mg/kg of test substance, $ED_{50}$ is the effective administered dose of test substance

| | | in vivo | |
| --- | --- | --- | --- |
| Formula | Example No. | po act. % | sc act. % |
| IA1 | 11 | 80 | tox |
| IA3 | 120 | 46 | 91 |
| IA4 | 126 | 79 | 76 |
| IA4 | 136 | 40 | tox |
| IA5 | 185 | 99.0 (10 mg/kg) | 99.95 |
| IA5 | 199 | 100 (10 mg/kg) | 99.97 |
| IA5 | 203 | 76 (10 mg/kg) | 90 |
| IA5 | 206 | 46 | 44 |
| IA8 | 210 | 82 | 99 |
| IA8 | 211 | 59 (10 mg/kg) | 92 |
| III | 251 | 40 | 74 |

The compounds of formula IA or IB and the pharmaceutically acceptable acid addition salts of the compounds of formula IA or IB can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions, or nasally.

The compounds of formula IA or IB and the pharmaceutically acceptable acid addition salts of the compounds of formula I can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active ingredient no carriers are, however, usually required in the case of soft gelatine capsules. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances.

Medicaments containing a compound of formula IA or IB or a pharmaceutically acceptable acid addition salt thereof and a therapeutically inert carrier are also an object of the present invention, as is a process for making them which comprises bringing one or more compounds of formula IA or IB and/or pharmaceutically acceptable acid addition salts thereof into a galenical administration form together with one or more therapeutically inert carriers.

In accordance with the invention compounds of formula IA or IB as well as their pharmaceutically acceptable acid addition salts can be used for the treatment or prevention of malaria and, respectively, for the production of corresponding medicaments. The dosage can vary within wide limits and will, of course, be fitted to the individual requirements in each particular case. In the case of oral administration the dosage lies in a range of about 10 mg to about 2.5 g per day of a compound of general formula IA or IB or the corresponding amount of a pharmaceutically acceptable acid addition salt thereof, although the upper limit can also be exceeded when this is found to be indicated.

In the following Examples, which illustrate the present invention but are not intended to limit its scope in any manner, all temperatures are given in degrees Celsius. The 250 MHz-$^1$H-NMR spectra were measured at room temperature; chemical shifts δ (ppm) relative to δ (TMS)=0.0 ppm.

The novel compounds of formula IA5 can be prepared as described below. All temperature are given in ° C.

EXAMPLE 164

(E)-2-[2-(1E,3E)-4-[4,5-Dimethoxy-2-nitro-phenyl)-buta-1,3-dienyl]-phenyl]-3-methoxy-acrylic acid methyl ester a) At room temperature, NaOCH$_3$ (335 mg, 6.19 mmol) was added to a solution of 1,3-dioxan-2-ylmethyltributylphosphoniumbromide (C. Spangler; R. McCoy, Synthetic communications, 18, 51, (1988)) (5.17 ml, 1 M in DMF, 5.71 mmol) and 4,5-dimethoxy-2-nitrobenzaldehyde (1.25 g, 4.76 mmol) in DMF (20 ml). After heating the mixture at 50° for overnight, the mixture was poured over water, and extracted with ether, washed with brine and dried over MgSO$_4$. The solvent was evaporated and the residue was dissolved in THF (100 ml) and treated with 2 N HCl (50 ml). After stirring the mixture at room temperature for 2 h, the THF was evaporated, and the yellow solid was filtered, and suspended in ether/ethylacetate 4:1. The suspension stirred at room temperature for 1 h, filtered and washed with ether to afford (E)-3-(4,5-dimethoxy-2-nitro-phenyl)-propenal (624 mg, 55%) as a yellow solid, m.p. 103–105°. IR (KBr): 1689, 1605 cm$^{-1}$. MS (EI): 237 (M).

b) At 0°, NaH (40 mg, 0.954 mmol) was added to a solution of (E)-2-[2-(dimethoxy-phosphorylmethyl)-phenyl]-3-methoxy-acrylic acid methyl ester (EP-203606) (250 mg, 0.79 mmol) in THF (5 ml). The mixture was stirred at room temperature for 30 min and treated with (E)-3-(4,5-dimethoxy-2-nitro-phenyl)-propenal (189 mg, 0.79 mmol) in CH$_2$Cl$_2$ (2 ml). After the mixture was stirred at room temperature for 3 h and refluxed for 1.5 h, the reaction mixture was cooled to room temperature and treated with CH$_3$CO$_2$H (1 ml). After stirring for 10 min at room temperature, the reaction mixture was extracted with ethylacetate, washed with NaHCO$_3$ solution, brine, water, and dried over MgSO$_4$. Evaporation of the solvent and chromatography (hexane/ethylacetate 1:1) gave (E)-2-[2-(1E,3E)-4-[4,5-dimethoxy-2-nitro-phenyl)-buta-1,3-dienyl]-phenyl]-3-methoxy-acrylic acid methyl ester (116 mg, 34%) as white solid, m.p. 198–200°. IR (KBr): 1710, 1630 cm$^{-1}$. MS (EI): 425 (M).

According to the procedure set forth in the preceding example, the following compounds were prepared:

EXAMPLE 165

(E)-2-[2-[(1E,3E)-4-(2,4-Dichloro-phenyl)-buta-1,3-dienyl]-phenyl]-3-methoxy-acrylic acid methyl ester m.p. 143–145°

IR (KBr): 1707, 1629 cm$^{-1}$, MS (EI): 388 (M)

EXAMPLE 166

Methyl (E and/or Z)-3-methoxy-2-[o-[(all-E)-4-(2-pyridyl)-1,3-butadienyl]-phenyl]acrylate m.p. 106–108°

EXAMPLE 167

Methyl (E and/or Z)-2-[o-[(all-E)-4-(2,3-dichloro-phenyl)-1,3-butadienyl]-phenyl]-3-methoxyacrylate m.p. 141–145°

EXAMPLE 168

Methyl (E and/or Z)-2-[o-[(all -E)-4-(2,3-difluorophenyl)-1,3-butadienyl]-phenyl]-3-methoxyacrylate m.p. 142–144°

EXAMPLE 169

Methyl (E and/or Z)-3-methoxy-2-[o-[(all-E)-4-(2-quinolinyl)-1,3-butadienyl]phenyl]acrylate m.p. 137–138°

EXAMPLE 170

Methyl (E and/or Z)-3-methoxy-2-[o-[(all-E)-4-(1-naphthyl)-1,3-butadienyl]-phenyl]acrylate m.p. 138–140°

EXAMPLE 171

Methyl (E and/or Z)-3-methoxy-2-[o-[(all-E)-4-(1-methylpyrrol-2-yl)-1,3-butadienyl]phenyl]acrylate m.p. 139–142°

EXAMPLE 172

Methyl (E and/or Z)-3-methoxy-2-[o-[(all-E)-4-(4-pyridyl)-1,3-butadienyl]-phenyl]acrylate
m.p. 175–177°

EXAMPLE 173

Methyl (E and/or Z)-2-[o-[(all-E)-4-(2-furyl)-1,3-butadienyl]phenyl]-3-methoxyacrylate
m.p. 136–137°

EXAMPLE 174

Methyl (E and/or Z)-3-methoxy-2-[o-[(all-E)-4-(2-thienyl)-1,3-butadienyl]-phenyl]acrylate
m.p. 142–145°

EXAMPLE 175

Methyl (E and/or Z)-3-methoxy-2-[o-[(all-E and/or Z)-4-(3-thienyl)-1,3-butadienyl]phenyl]acrylate
m.p. 194–195°

EXAMPLE 176

Methyl (E and/or Z)-3-methoxy-2-[o-[(all-E)-4-(3-quinolinyl)-1,3-butadienyl]phenyl]-3-methoxyacrylate
m.p. 173–175°

EXAMPLE 177

Methyl (E)-3-methoxy-2-[o-[(all-E)-4-(alpha,alpha,alpha-trifluoro-p-tolyl)-1,3-butadienyl]-phenyl]acrylate
m.p. 190–191°

EXAMPLE 178

Methyl (E)-2-[o-[(all-E)-4-(p-fluorophenyl)-1,3-butadienyl]phenyl]-3-methoxyacrylate
m.p. 156–157°

EXAMPLE 179

Methyl (E)-2-[o-[(all-E)-4-(o-ethoxyphenyl)-1,3-butadienyl]phenyl]-3-methoxyacrylate
m.p. 152–153°

EXAMPLE 180

Methyl (E)-2-[o-[(all-E)-4-(2-chloro-6-fluorophenyl)-1,3-butadienyl]phenyl]-acrylate
m.p. 165°

EXAMPLE 181

Methlyl (E)-3-methoxy-2-[o-[(all-E)-4-(alpha,alpha,alpha-trifluoro-m-tolyl)-1,3-butadienyl]phenyl]acrylate
m.p. 152–153°

EXAMPLE 182

Methyl (E)-2-[o-[(all-E)-4-(3-furyl)-1,3-butadienyl]phenyl]-3-methoxyacrylate
m.p. 174–175°

EXAMPLE 183

Methyl (E)-2-[o-[(all-E)-4-[2-(-p-chloro-phenyl)-4-thiazolyl]-1,3-butadienyl]-phenyl]-3-methoxyacrylate
m.p. 167–171°

EXAMPLE 184

Methyl (E)-2-[o-[(all-E)-4-(o-chlorophenyl)-1,3-butadienyl]phenyl]acrylate
m.p. 158–162°

EXAMPLE 185

Methyl (E)-3-methoxy-2-[o-[(all-E)-4-(alpha,alpha,alpha-trifluoro-tolyl)-1,3-butadienyl]-phenl]acrylate
m.p. 148–149°

EXAMPLE 186

Methyl (E)-2-[o-[(all-E)-4-(m-fluorophenyl)-1,3-butadienyl]phenyl]-3-methoxyacrylate
IR (KBr): 1705, 1628 cm$^{-1}$, MS (EI): 338 (M)

EXAMPLE 187

Methyl (E)-3-methoxy-2-[o-[(all-E)-4-(5-phenyl-4-thiazolyl)-1,3-butadienyl]-phenyl]acrylate
m.p. 167°

EXAMPLE 188

Methyl (E)-2-[o-[(all-E)-4-(5-bromo-2-thienyl)-1,3-butadienyl]phenyl]-3-methoxyacrylate
m.p. 160–161°

EXAMPLE 189

Methyl (E)-3-methoxy-2-[o-[(all-E)-4-(-p-methoxyphenyl)-1,3-butadienyl]-phenyl]acrylate
m.p. 164–166°

EXAMPLE 190

Methyl (E)-3-methoxy-2-[o-[(all-E)-4-[3-methoxybenzo[b]thiophen-2-yl]-1,3-butadienyl]phenyl]acrylate
m.p. 202–203°

EXAMPLE 191

Methyl (E)-3-methoxy-2-[o-[(all-E)-3-(2-thiazolyl)-1,3-butadienyl]phenyl]-acrylate
m.p. 131–133°

EXAMPLE 192

Methyl (E)-3-methoxy-2-[o-[(all-E)-4-(5-methyl-2-thienyl)-1,3-butadienyl]-phenyl]acrylate
m.p. 131–133°

EXAMPLE 193

Methyl (E)-3-methoxy-2-[o-[(all-E)-4-(3-methyl-2-thienyl)-1,3-butadienyl]-phenyl]acrylate
m.p. 168°

EXAMPLE 194

Methyl (E)-3-methoxy-2-[o-[4-(2-naphthyl)-1,3-butadienyl]-phenyl]acrylate
m.p. 172°

EXAMPLE 195

Methyl (E)-2-[o-[(all-E)-4-benzo[b]thiophen-2-yl-1,3-butadienyl]phenyl]-3-methoxy-acrylate
m.p. 223–225°

EXAMPLE 196

Methyl (E)-2-[o-[(all-E)-4-benzo[b]thiophen-3-yl-1,3-butadienyl]phenyl]-3-methoxy-acrylate m.p. 157°

EXAMPLE 197

Methyl (E)-3-methoxy-2-[o-[(all-E)-4-phenyl-1,3-butadienyl]-phenyl]acrylate m.p. 165–167°

EXAMPLE 198

(E)- or (Z)-2-[2-[4-(3,5-bis-trifluoromethyl-phenyl)-buta-1,3-dienyl]phenyl]-3-methoxy-acrylic acid methyl ester IR (KBr): 1703, 1630 cm$^{-1}$

MS (EI): 456 (M)

EXAMPLE 199

(E)- or (Z)-2-[2-[4-(2,4-bis-trifluoromethyl-phenyl)-buta-1,3-dienyl]phenyl]-3-methoxy-acrylic acid methyl ester m.p. 176–177°

IR (KBr): 1703, 1630 cm$^{-1}$

MS (EI): 456 (M)

EXAMPLE 200

Methyl-2-[o-[(all-E)-4-(m-bromophenyl)-1,3-butadienyl]phenyl]-3-methoxy-acrylic

IR (KBr): 1701, 1626 cm$^{-1}$

MS (EI): 399 (M)

EXAMPLE 201

Methyl (E)-2-[o-[(all-E)-4-(p-chlorophenyl)-1,3-butadienyl]-phenyl]-3-methoxyacrylate m.p. 209°

EXAMPLE 202

Methyl (E)-2-[o-[(all-E)-4-(m-chlorophenyl)-1,3-butadienyl]phenyl]-3-methoxyacrylate m.p. 121–122°

EXAMPLE 203

Methyl (E)-2-[o-[(all-E)-4-(o-bromophenyl)-1,3-butadienyl]phenyl]-3-methoxyacrylate m.p. 150–151°

EXAMPLE 204

Methyl (E)-3-methoxy-2-[o-[(all-E)-4-(3,4,5-trimethoxyphenyl)-1,3-butadienyl]phenyl]acrylate m.p. 98–109°

EXAMPLE 205

Methyl (E)-2-[o-[(all-E)-4-(p-tert-butylphenyl)-3-methyl-1,3-butadienyl]-phenyl]3-methoxyacrylate IR (KBr): 1709, 1632 cm$^{-1}$

MS (EI): 390 (M)

EXAMPLE 206

(Z)- or (E)-Methoxyimino-[2-[(1E,2E)-4-(2-trifluoromethylphenyl)-buta-1,3-dienyl]-phenyl]-acetic acid methyl ester a) At 24°, Bu$_3$SnH (0.56 ml, 2.1 mmol) was added to a solution of (2-ethynyl-phenyl)-methoxyimino-acetic acid methyl ester (151 mg, 0.7 mmol) and AIBN (cat.) in toluene (0.5 ml). After the mixture was stirred at 80° for 3.5 h, solvent was evaporated under reduced pressure and chromatography (hexane/ethylacetate 9:1) gave methoxyimino-[2-(E,Z)-(2-tributylstannanyl-vinyl)-phenyl]-acetic acid methyl ester (1:1 mixture) (155 mg, 44%) as a yellowish liquid. IR (KBr): 1731, 1600 cm$^{-1}$. MS (EI): 508 (M).

b) A solution of 1-(2,2-dibromo-vinyl)-2-trifluoromethyl-benzene (989 mg, 3 mmol) and Et)$_2$POH (0.75 ml, 6 mmol) in Et$_3$N (0.83 ml, 6 mmol) was stirred at 5° for 4 h. Hexane was added, and stirred for further 10 min. The mixture was extracted with hexane, washed with brine and dried over Na$_2$SO$_4$. Evaporation of the solvent and chromatography (hexane) gave 1-(2-bromo-vinyl)-2-trifluoromethyl-benzene (674 mg, 90%) as a colorless liquid. IR (KBr): 1600, 940 cm$^{-1}$. MS (EI): 251 (M).

c) At 24°, Pd[PPh$_3$]$_4$ (21 mg, 0.02 mmol) was added to a solution of 1-(1-bromo-vinyl)-2-trifluoromethyl-benzene (151 mg, 0.6 mmol) and methoxy-imino-[2-(E,Z)-(2-tributylstannanyl-vinyl)-phenyl]-acetic acid methyl ester (304 mg, 0.6 mmol) in toluene (5 ml). The mixture was stirred at 110° for 5 h, cooled to room temperature, extracted with toluene, washed with brine, and dried over Na$_2$SO$_4$. Evaporation of the solvent and chromatography (hexane/ethylacetate 3:2) gave (Z)- or (E)-methoxyimino-[2-[(lE,2E)-4-(2-trifluoromethylphenyl)-buta-1,3-dienyl]-phenyl]-acetic acid methyl ester (48 mg, 21%) as brown oil. IR (KBr): 1734, 1610 cm$^{-1}$. MS (EI): 389 (M).

EXAMPLE 251 (III)

(E)-3-Methoxy-2-{(E)-2-[(R)- and (S)-3-(tetrahydro-pyran-2-yloxy}-propenyl]-phenyl}-acrylic acid methyl ester (active intermediate)

At 24°, Pd[PPh$_3$]$_4$ (58 mg, 0.05 mmol) was added to a solution of (E)-tributyl-[3-(R)- and (S)-(tetrahydro-pyran-2-yloxy)-propenyl]-stannane (2.2 g, 5.1 mmol) (E. J. Corey; J. W. Suggs, J. Org. Chem. 40, 2554, (1975)) and (E)-2-(2-bromo-phenyl)-3-methoxy acid methyl ester (1.38 mg, 5.1 mmol) (EP 0307101 A2 890315) in toluene (20 ml). The mixture was stirred at 110° for 2 days, cooled to room temperature, extracted with toluene, washed with brine, and dried over Na$_2$SO$_4$. Evaporation of the solvent and chromatography (hexane/ethylacetate 9:1) gave (E)-3-methoxy-2-[(E)-2-[(R)- and (S)-3-(tetrahydro-pyran-2-yloxy)-propenyl]-phenyl]-acrylic acid methyl ester (884 mg, 52%) as a white solid, m.p. 66–68°. IR (Br): 1711, 1633 cm$^{-1}$. MS (EI): 216 (M-MeOH-Dihydropyrane).

EXAMPLE 252 (IV)

(E)-2-[2-(3-Hydroxy-propenyl)-phenyl]-3-methoxy-acrylic acid methyl ester (active intermediate)

At 24°, toluene-4-sulfonic acid monohydrate (1.11 g, 0.4 mmol) was added to a solution of (E)-3-methoxy-2-[(E)-2-[(R)- and (S)-3-(tetrahydro-pyran-2-yloxy)-propenyl]-phenyl]-acrylic acid methyl ester (4.866 g, 14 mmol) in ethanol (70 ml). After the mixture was stirred for 6 h and neutralized with K$_2$CO$_3$ solution, the solvent was evaporated and the crude was dissolved in ethylacetate, washed with brine, water, and dried over Na$_2$SO$_4$. Evaporation of the solvent gave (E)-2-[2-(3-hydroxy-propenyl)-phenyl]-3-methoxy-acrylic acid methyl ester (3.4 g, 93%) as a white solid, m.p. 78–80°. IR (YBr): 1683, 1619 cm$^{-1}$. MS (EI): 216 (M-MeOH).

EXAMPLE A (E)-2-[2-(1E,3E)-4-[4,5-dimethoxy-2-nitro-phenyl)-buta-1,3-dienyl]-phenyl]-3-methoxyacrylic acid methyl ester can be formulated as the active ingredient according to methods known per se to give pharmaceutical preparations of the following composition:

| 1. 500 mg tablets | |
|---|---|
| Active ingredient | 500 mg |
| Powd. lactose | 149 mg |
| Polyvinylpyrrolidone | 15 mg |
| 2. Dioctyl sodium sulphosuccinate | 1 mg |
| Na carboxymethylstareh | 30 mg |
| Magnesium stearate | 5 mg |
| | 700 mg |
| 2. 50 mg tablets | |
| Active ingredient | 50 mg |
| Powd. lactose | 50 mg |
| Microcrystalline cellulose | 82 mg |
| Na carboxymethylstarch | 15 mg |
| | 200 mg |
| 3. 100 mg capsules | |
| Active ingredient | 100.0 mg |
| Powd. lactose | 104.7 mg |
| Corn starch | 70.0 mg |
| Hydroxypropylmethylcellulose | 10.0 mg |
| Dioctyl sodium sulphosuccinate | 0.3 mg |
| Talc | 12.0 mg |
| Magnesium stearate | 3.0 mg |
| | 300.0 mg |
| 4. 500 mg suppositories | |
| Active ingredient | 500 mg |
| Suppository mass | ad 2000 mg |
| 5. 100 mg soft gelatine capsules | |
| Active ingredient | 100 mg |
| Medium chain triglyceride | 300 mg |
| | 400 mg |

What is claimed is:

1. A compound of formula

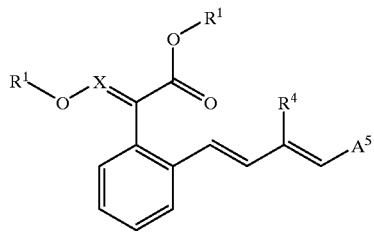

IA5 wherein

R¹ is lower alkyl;

X is N or CH;

R⁴ is hydrogen or lower alkyl; and

A⁵ is phenyl which is unsubstituted or substituted by one or more substituents, selected from lower alkyl, lower alkoxy, $NO_2$, halogen, cyano or $CF_3$; pyridin-2-yl; pyridin-4-yl; quinolin-2-yl; quinolin-3-yl; naphthyl; pyrrol-2-yl, which is unsubstituted or substituted by lower alkyl; furan-2-yl, furan-3-yl; thien-2-yl; thien-3-yl, , which is unsubstituted or substituted by halogen or lower alkyl; thiazol-2-yl, which is unsubstituted or substituted by $C_6H_4Cl$; thiazol-4-yl, which is unsubstituted or substituted by phenyl; benzo[b]thiophen-2-yl, which is unsubstituted or substituted by halogen; or benzo[b]thiophen-3-yl;

as well as the stereoisomers and racemates thereof, and their pharmaceutically acceptable salts.

2. The compound of claim 1, wherein R¹ is methyl.

3. The compound of claim 2, wherein R⁴ is hydrogen.

4. The compound of claim 3, wherein X is CH.

5. The compound of claim 4, wherein A⁵ is phenyl which is substituted by one or more substitutents selected from lower alkyl, lower alkoxy, $NO_2$, halogen, cyano, or $CF_3$.

6. The compound of claim 5, (E)-2-[2-[(1E,3E)-4-(2-Chloro-3,4-dimethoxyphenyl)-buta-1,3-dienyl]-phenyl]-3-methoxy-acrylic acid methyl ester.

7. The compound of claim 5, (E)-2-[2-[(1E,3E)-4-(2-bromo-4,5-dimethoxy-phenyl)-buta-1,3-dienyl]-phenyl]-3-methoxy-acrylic acid methyl ester.

8. The compound of claim 5, (E)-2-[2-[(1E,3E)-4-(2-cyano-phenyl)-buta-1,3-dienyl]-3-methoxy-acrylic acid methyl ester.

9. The compound of claim 5, (E)-3-methoxy-2-[2-[(1E,3E)-4-(3-methoxy-2-nitro-phenyl)-buta-1,3-dienyl]-phenyl]-acrylic acid methyl ester.

10. The compound of claim 5, (E)-2-[2-[(1E,3E)-4-(4-fluoro-2-trifluoromethyl-phenyl)-buta-1,3-dienyl]-phenyl]-3-methoxy-acrylic acid methyl ester.

11. The compound of claim 5, (E)-2-[2-[(1E,3E)-4-(4-tert-butyl-phenyl)-buta-1,3-dienyl]-phenyl]-3-methoxy-acrylic acid methyl ester.

12. The compound of claim 5, (E)-2-[2-[(1E,3E)-4-(2-chloro-4-fluoro-phenyl)-buta-1,3-dienyl]-phenyl]-3-methoxy-acrylic acid methyl ester.

13. The compound of claim 5, (E)-2-[2-[(1E,3E)-4-(2,4-diuoro-phenyl)-buta-1,3-dienyl]-phenyl]-3-methoxy-acrylic acid methyl ester.

14. The compound of claim 5, (E)-2-[2-[(1E,3E)-4-(2-chloro-4-methyl-phenyl)-buta-1,3-dienyl]-phenyl]-3-methoxy-acrylic acid methyl ester.

15. The compound of claim 5, (E)-2-[2-[(1E,3E)-4-(2,4-dimethyl-phenyl)buta-1,3-dienyl]-phenyl]-3-methoxy-acrylic acid methyl ester.

16. The compound of claim 5, (E)-2-[2-[(1E,3E)-4-(2-fluoro-4-trifluoromethyl-phenyl-buta- 1,3-dienyl]-phenyl]-3-methoxy-acrylic acid methyl ester.

17. The compound of claim 5, Methyl (E)-3-methoxy-2-[o-[(all-E)-4-(alpha,alpha,alpha-trifluoro-tolyl)-1,3-butadienyl]phenyl]acrylate.

18. The compound of claim 5, (E)- or (Z)-2-[2-[4-(2,4-bis-trifluoromethyl-phenyl)-buta-1,3-dienyl]phenyl]-3-methoxy-acrylic acid methyl ester.

19. The compound of claim 5, Methyl(E)-2-[o-[(all-E)-4-(o-bromophenyl)-1,3-butadienyl]phenyl]-3-methoxyacrylate.

20. The compound of claim 3, wherein X is N.

21. The compound of claim 20, (Z)- or (E)-Methoxyimino-[2-[(1E,2E)-4-(2-truoromethylphenyl)-buta-1,3-dienyl]-phenyl]-acetic acid methyl ester.

* * * * *

UNITED STATES PATENT AND TRADEMARK OFFICE
CERTIFICATE OF CORRECTION

PATENT NO.    : 6,084,120  
DATED         : July 4, 2000  
INVENTOR(S)   : Alzeer et al.

Page 1 of 1

It is certified that error appears in the above-identified patent and that said Letters Patent is hereby corrected as shown below:

Title page,
- Item [56], replace " 2 670 782" with -- 2 670 781 --.

Signed and Sealed this

Eighth Day of January, 2002

Attest:

Attesting Officer

JAMES E. ROGAN  
Director of the United States Patent and Trademark Office